US012698331B2

(12) United States Patent
Bruhns et al.

(10) Patent No.: US 12,698,331 B2
(45) Date of Patent: Aug. 4, 2026

(54) ANTIBODY BLOCKING HUMAN FCγRIIIA AND FCγRIIIB

(71) Applicants: INSTITUT PASTEUR, Paris (FR); CENTRE NATIONAL DE LA RECHERCHE SCIENTIFIQUE (CNRS), Paris (FR); INSERM (Institut National de la Sante et de la Recherche Medicale), Paris (FR)

(72) Inventors: Pierre Bruhns, Paris (FR); Odile Madeleine Richard-Le Goff, Paris (FR); Patrick Evan England, Le Perreux-sur-Marne (FR); Sylviane Hoos, Sceaux (FR); Friederike Jonsson, Antony (FR)

(73) Assignees: INSTITUT PASTEUR, Paris (FR); CENTRE NATIONAL DE LA RECHERCHE SCIENTIFIQUE (CNRS), Paris (FR); INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 1091 days.

(21) Appl. No.: 17/783,894

(22) PCT Filed: Dec. 10, 2020

(86) PCT No.: PCT/EP2020/085495
§ 371 (c)(1),
(2) Date: Jun. 9, 2022

(87) PCT Pub. No.: WO2021/116277
PCT Pub. Date: Jun. 17, 2021

(65) Prior Publication Data
US 2023/0227559 A1 Jul. 20, 2023

(30) Foreign Application Priority Data

Dec. 10, 2019 (EP) .................................... 19306617

(51) Int. Cl.
| | |
|---|---|
| *C07K 16/28* | (2006.01) |
| *A61P 37/06* | (2006.01) |
| *G01N 33/569* | (2006.01) |
| *A61K 39/00* | (2006.01) |

(52) U.S. Cl.
CPC ............ *C07K 16/283* (2013.01); *A61P 37/06* (2018.01); *G01N 33/56972* (2013.01); *A61K 2039/505* (2013.01); *G01N 2333/70535* (2013.01)

(58) Field of Classification Search
None
See application file for complete search history.

(56) References Cited

U.S. PATENT DOCUMENTS

| | | | | |
|---|---|---|---|---|
| 7,728,114 B2 * | 6/2010 | Mach | ......................... | A61P 1/04 |
| | | | | 530/388.22 |
| 2018/0305453 A1 * | 10/2018 | Lazarus | .................. | A61P 37/06 |

FOREIGN PATENT DOCUMENTS

| | | |
|---|---|---|
| WO | 2003/101485 A1 | 12/2003 |
| WO | 2018/158350 A1 | 9/2018 |
| WO | 2019/198051 A2 | 10/2019 |

OTHER PUBLICATIONS

Harlow (Antibodies, A Laboratory Manual, Cold Spring Harbor laboratory, 1988, pp. 37-47 and 55-59). (Year: 1988).*
Meyer et al. (British Journal of Haematology, 2018, 180, 808-820, supplemental pp. 1-5). (Year: 2018).*
Edwards et al. (J. Mol. Biol. (2003) 334, 103-118). (Year: 2003).*
Vajdos et al. (J Mol Biol. Jul. 5, 2002;320(2):415-28). (Year: 2002).*
Bedouelle et al. (FEBS J. Jan. 2006;273(1):34-46). (Year: 2006).*
Brown et al. (J Immunol. May 1, 1996;156(9):3285-91). (Year: 1996).*
Colman (Research in Immunology, 145:33-36, 1994). (Year: 1994).*
Rudikoff et al. (Proc. Natl. Acad. Sci. USA, 79: 1979-1983, Mar. 1982). (Year: 1992).*
Bruce Booth, "Human Antibody Discovery: Of Mice And Phage," pp. 1-7, 2017. (Year: 2017).*
Using Antibodies: A Laboratory Manual, Edward Harlow, Cold Spring Harbor Laboratory Press, 1999, pp. 28-29. (Year: 1999).*
Altschul et al., Gapped BLAST and PSI-BLAST: a new generation of protein database search programs, Nucleic Acids Res. 1997, 25(17), 3389-3402.

(Continued)

*Primary Examiner* — Zachary S Skelding

(74) *Attorney, Agent, or Firm* — Arrigo, Lee, Guttman & Mouta-Bellum LLP

(57) ABSTRACT

The present invention relates to novel antibodies, in particular murine monoclonal antibodies, chimeric and humanized, that are able to block specifically the human IgG receptors FcγRIIIA (CD16A) and FcγRIIIB (CD16B) as well as the amino and nucleic acid sequences coding for such antibodies. The invention also comprises the use of such antibodies or of fragments thereof as a medicament for the preventive and/or therapeutic treatment of diseases involving CD16, like autoimmune diseases, inflammatory disorders, allergies and infections, without inducing any adverse effects. In particular, these antibodies and fragments can prevent or treat anti-drug idiopathic thrombocytopenic purpura (ITP), rheumatoid arthritis (RA) and autoimmune hemolytic anemia (ANA).

13 Claims, 12 Drawing Sheets

Figure 1:
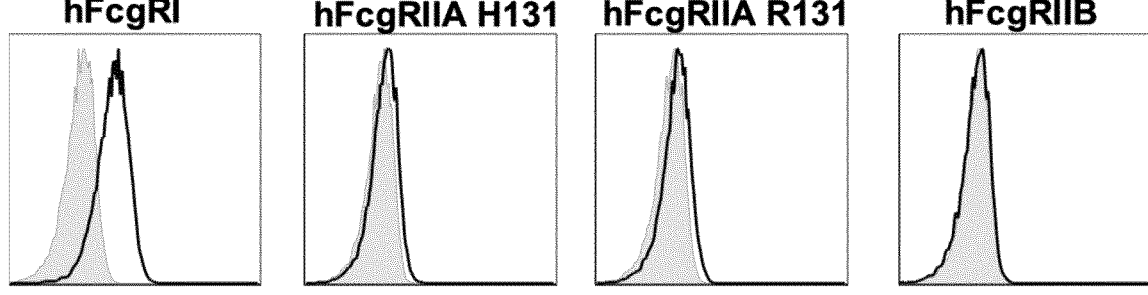
Figure 1:
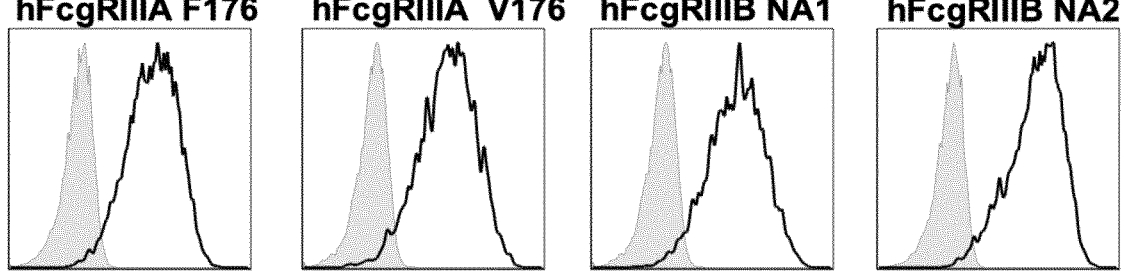
Figure 1:
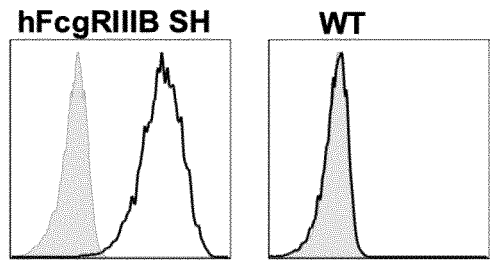

Specification includes a Sequence Listing.

(56)          References Cited

OTHER PUBLICATIONS

Beutier et al. Platelets expressing IgG receptor FcgammaRIIA/CD32A determine the severity of experimental anaphylaxis. Sci Immunol. 2018, 3(22), eaan5997, 1-11.
Breunis et al. Copy number variation of the activating FCGR2C gene predisposes to idiopathic thrombocytopenia purpura. Blood. 2008,111(3), 1029-1038.
Bruhns et al. Specificity and affinity of human Fcγ receptors and their polymorphic variants for human IgG subclasses. Blood, 2009;113(16), 3716-3725.
Bruhns P and Jonsson F. Mouse and human FcR effector functions. Immunol Rev. 2015, 268(1), 25-51.
Bussel JB et al. GMA161 Treatment of Refractory ITP: Efficacy of Fcγ-RIII Blockade. Blood. 2006, 108(11), 1074.
Chaturvedi et al. Splenectomy for immune thrombocytopenia: down but not out. Blood. 2018, 131(11), 1172-1182.
Chong BH. Primary immune thrombocytopenia: understanding pathogenesis is the key to better treatments. J Thromb Haemost. 2009, 7(2), 319-321.
Clarkson et al. Treatment of refractory immune thrombocytopeniarpura with an anti-Fc gamma-receptor antibody. N Engl J Med. 1986, 314(19), 1236-1239.
Dall'Acqua et al. Increasing the affinity of a human IgG1 for the neonatal Fc receptor: biological consequences. J Immunol , 2002, 169: 5171-5180.
Dayhoff et al. A model of evolutionary change in proteins. Atlas of Protein Sequence and Structure, Natl. Biomed. Res. 1978, 5(3), 345-352.
Finkelman FD. Anaphylaxis: lessons from mouse models. J Allergy Clin Immunol. 2007, 120(3),506-515.
Flaherty et al. Nonclinical evaluation of GMA161—an antihuman CD16 (FcgammaRIII) monoclonal antibody for treatment of autoimmune disorders in CD16 transgenic mice. Toxicol Sci. 2012, 125(1), 299-309.
Fleit et al. Human neutrophil Fc gamma receptor distribution and structure. Proc Natl Acad Sci USA. 1982, 79(10), 3275-3279.
Foster et al. Polymorphisms in inflammatory cytokines and Fcγ receptors in childhood chronic immune thrombocytopenia purpura: a pilot study. British Journal of Haematology, 2001, 113, 596-599.
Fujimoto et al. Involvement of Fcγ receptor polymorphism in the therapeutic response of idiopathic thrombocytopenia purpura. British Journal of Haematology, (2001) 115, 125-130.
Gillis et al. Contribution of Human FcgammaRs to Disease with Evidence from Human Polymorphisms and Transgenic Animal Studies. Front Immunol, 2014, 5(254), 1-13.
Gillis et al. Anaphylaxis (Immediate Hypersensitivity): From Old to New Mechanisms(Immediate Hypersensitivity): From Old to New Mechanisms, Fig 2. Encyclopedia of Inflammatory Diseases. 2015. p. 4.
Gillis et al. Mechanisms of anaphylaxis in human low-affinity IgG receptor locus knock-in mice. J Allergy Clin Immunol. 2017, 139(4), 1253-1265.
Henikoff et al. Amino acid substitution matrices from protein blocks. Proc. Natl. Acad. Sci. USA, 1992, 89, 10915-10919.
Kistanguri and McCrae. Immune thrombocytopenia. Hematol Oncol Clin North Am. 2013, 27(3), 495-520.
Lee CH et al., An engineered human Fc domain that behaves like a pH-toggle switch for ultra-long circulation persistence. Nat Commun. 2019, 10(1), 5031, 1-11.
Efranc, M.-P., et al., IMGT unique numbering for MHC groove G-DOMAIN and MHC superfamily (MhcSF) G-LIKE-DOMAIN. Dev. Comp. Immunol., (2003), 27, 917-938.
Li et al. Desialylation is a mechanism of Fc-independent platelet clearance and a therapeutic target in immune thrombocytopenia. Nat Commun. 2015, 6(7737), 1-16.
Najean et al. The site of destruction of autologous 111In-labelled platelets and the efficiency of splenectomy in children and adults with idiopathic thrombocytopeniaurpura: a study of 578 patients with 268 splenectomies. Br J Haematol. 1997, 97(3), 547-550.
Nakar et al. 3G8 and GMA161, Anti FcγRIII Inhibitory Monoclonal Antibodies in the Treatment of Chronic Refractory ITP. (Summary of 2 Pilot Studies). Blood. 2009, 114(22), 2404, p. 1-7.
Portielje et al. Morbidity and mortality in adults with idiopathic thrombocytopeniarpura. Blood. 2001, 97(9), 2549-2554.
Rodeghiero et al. Standardization of terminology, definitions and outcome criteria in immune thrombocytopenic purpura of adults and children: report from an international working group. Blood. 2009;113(11), 2386-2393.
Shields, et al. High resolution mapping of the binding site on human IgG1 for Fc gamma RI, Fc gamma RII, Fc gamma RIII, and FcRn and design of IgG1 variants with improved binding to the Fc gamma R. J Biol Chem, 2001, 276(9), 6591-6604.
Zalevsky et al. Enhanced antibody half-life improves in vivo activity. Nat Biotechnol. 2010, 28(2), 157-159.
Feng J et al. Design and assembly of anti-CD16 ScFv antibody with two different linker peptides. Journal of Immunological Methods, 2003, 282, 33-43.
Li et al. Recombinant CD16A-Ig forms a homodimer and cross-blocks the ligand binding functions of neutrophil and monocyte Fcgamma receptors, Molecular Immunology, 2001, 38(7), 527-538.
Breunis et al. Copy number variation at the FCGR locus includes FCGR3A, FCGR2C and FCGR3B but not FCGR2A and FCGR2B. Human Mutation: Mutation in Brief, 2009, 1063, E640-650.

* cited by examiner hFcgRIIIA F176 hFcgRIIIA V176 hFcgRIIIB NA1 hFcgRIIIB NA2 hFcgRIIIB SH

A

3G4 hIgG1 $N_{297}$A format

- ● hFcγR$^{KI}$ - 3G4 hIgG1 $N_{297}$A format
- ■ hFcγR$^{KI}$- hIgG1 Herceptin
- △ mFcγR$^{null}$- 3G4 hIgG1 $N_{297}$A format

B

3G8 hIgG1

- ● hFcγR$^{KI}$ - 3G8 hIgG1
- ■ hFcγR$^{KI}$- hIgG1 Herceptin
- △ mFcγR$^{null}$- 3G8 hIgG1

Figure 3:
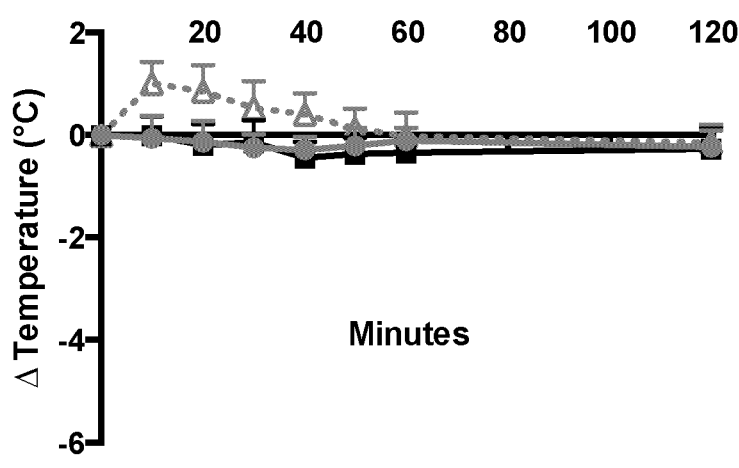
Figure 3:
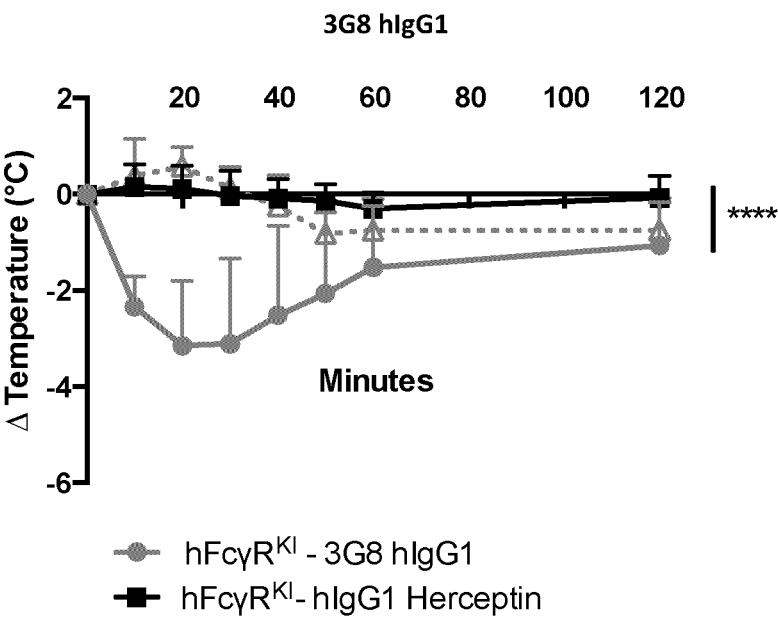

Figure 3 (continuation)
C
3G8 hIgG1 N$_{297}$A format
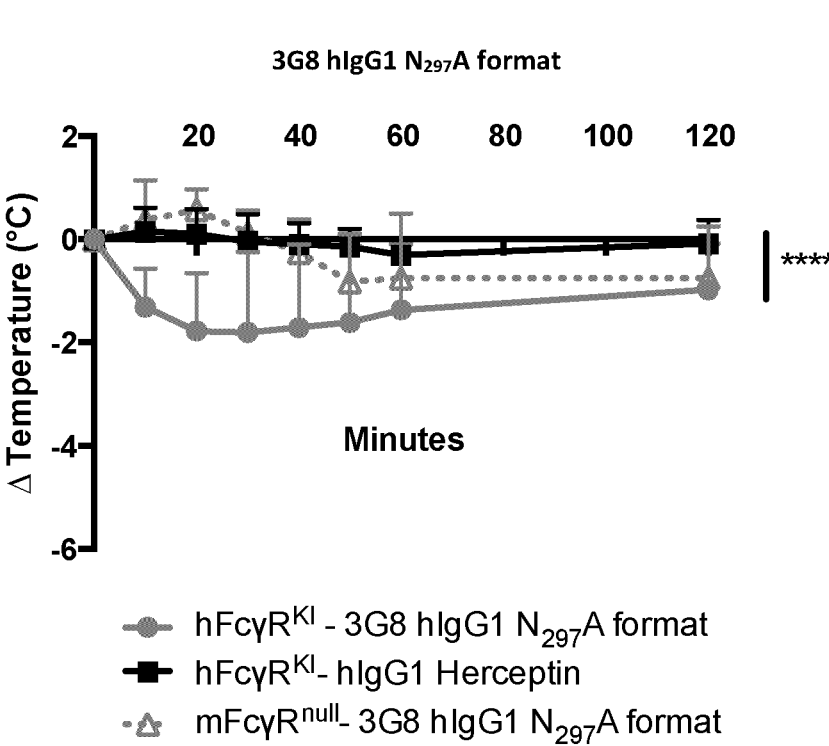
- hFcγR$^{KI}$ - 3G8 hIgG1 N$_{297}$A format
- hFcγR$^{KI}$- hIgG1 Herceptin
- mFcγR$^{null}$- 3G8 hIgG1 N$_{297}$A format

A

B

Figure 4:
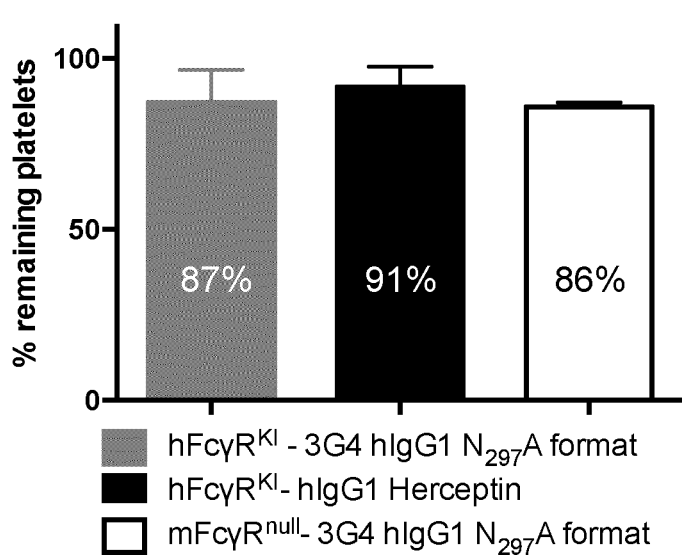
Figure 4:
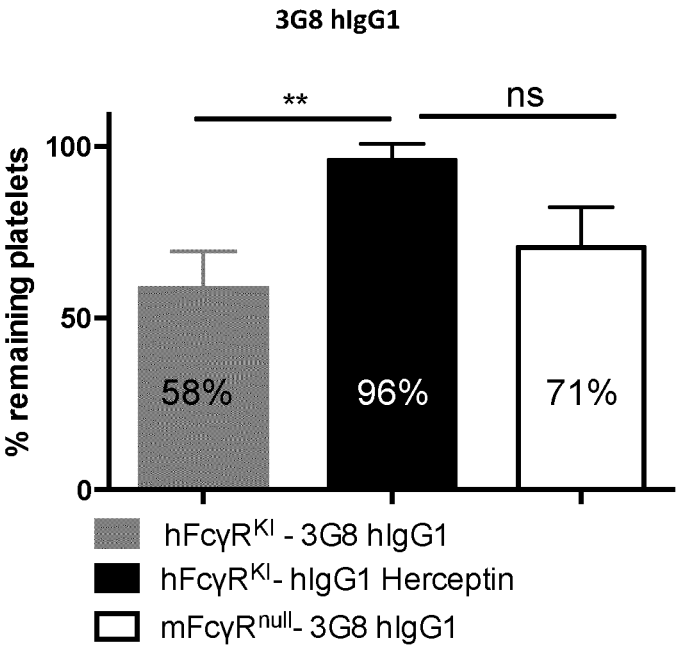

Figure 4 (continuation)
C
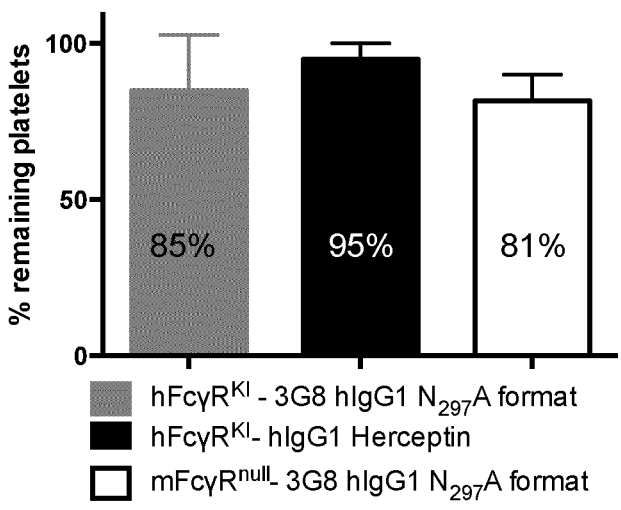
3G8 hIgG1 $N_{297}A$ format
hFcγR$^{KI}$ – 3G8 hIgG1 $N_{297}A$ format
hFcγR$^{KI}$– hIgG1 Herceptin
mFcγR$^{null}$– 3G8 hIgG1 $N_{297}A$ format

A

3G4 hIgG1 $N_{297}$A format3G8 hFcγR$^{KI}$ - 3G4 hIgG1 $N_{297}$A format hFcγR$^{KI}$- hIgG1 Herceptin mFcγR$^{null}$- 3G4 hIgG1 $N_{297}$A format

B

3G8 hIgG1 hFcγR$^{KI}$ - 3G8 hIgG1 hFcγR$^{KI}$- hIgG1 Herceptin mFcγR$^{null}$- 3G8 hIgG1

Figure 5:
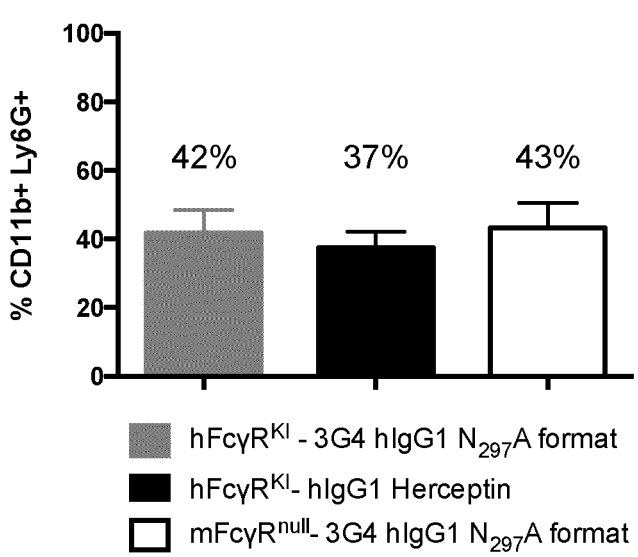
Figure 5:
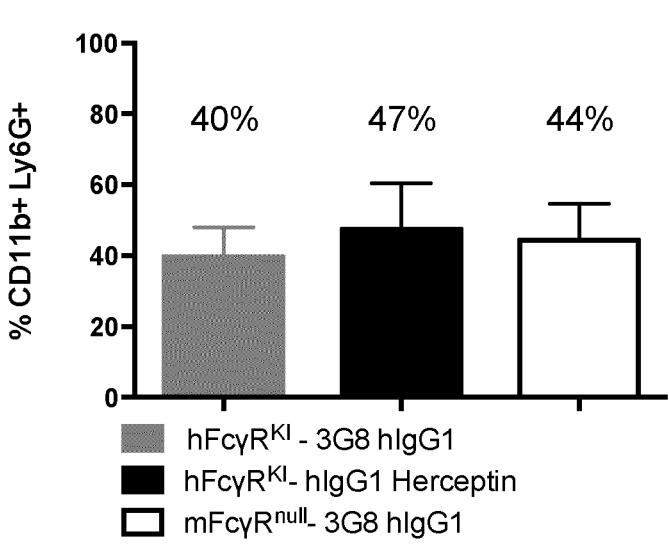

Figure 5 (continuation)
C
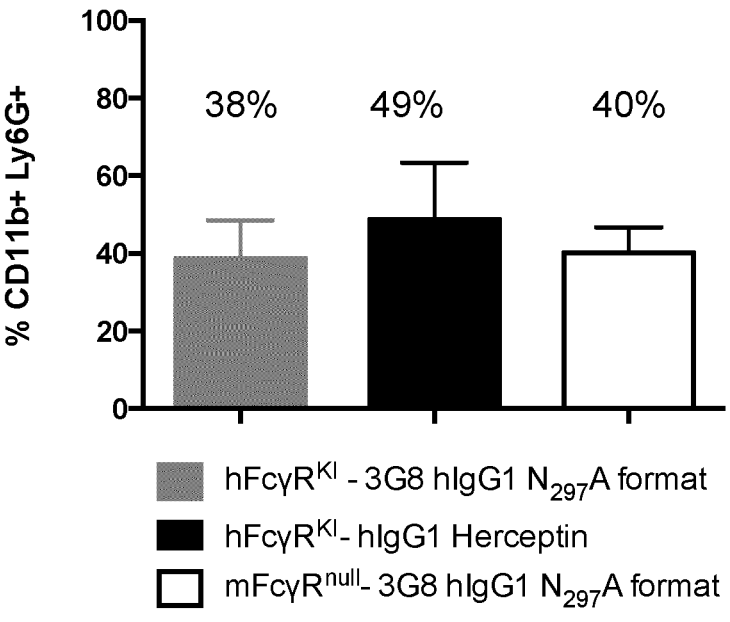
3G8 hIgG1 $N_{297}A$ format

A

B

Figure 6:
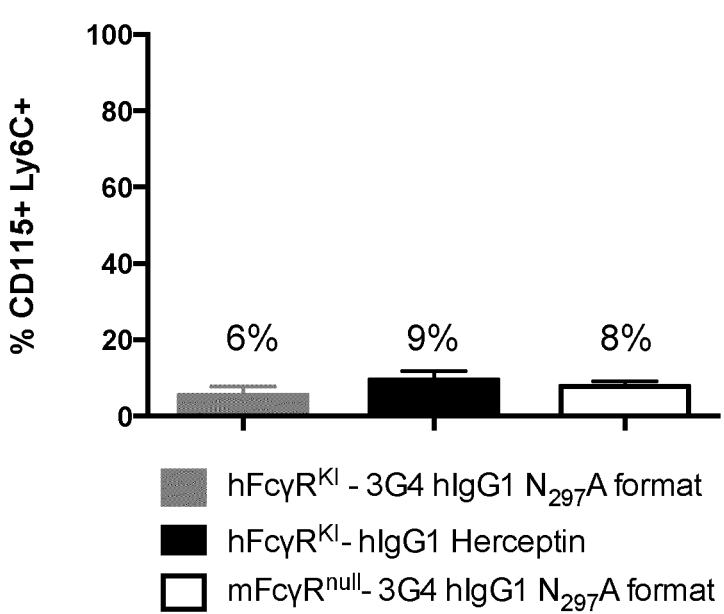
Figure 6:
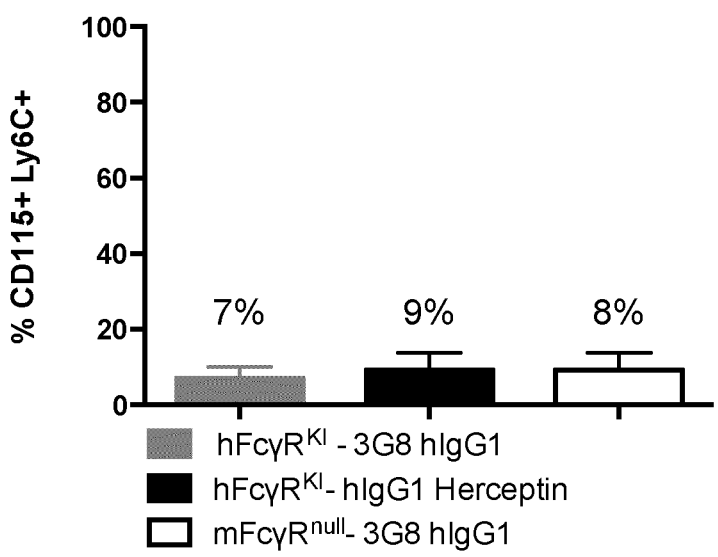

Figure 6 (continuation)
C
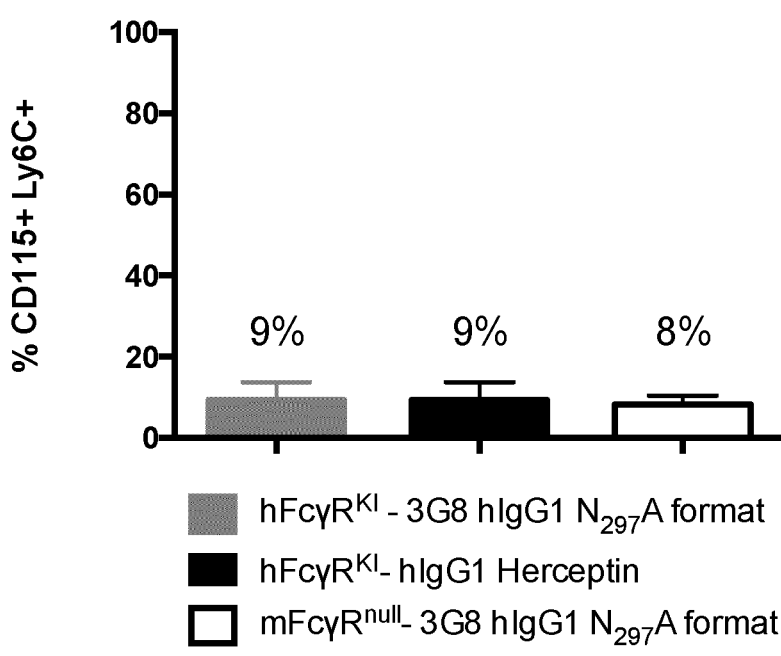
3G8 hIgG1 $N_{297}$A format
hFcγR$^{KI}$ - 3G8 hIgG1 $N_{297}$A format
hFcγR$^{KI}$- hIgG1 Herceptin
mFcγR$^{null}$- 3G8 hIgG1 $N_{297}$A format
Figure 7
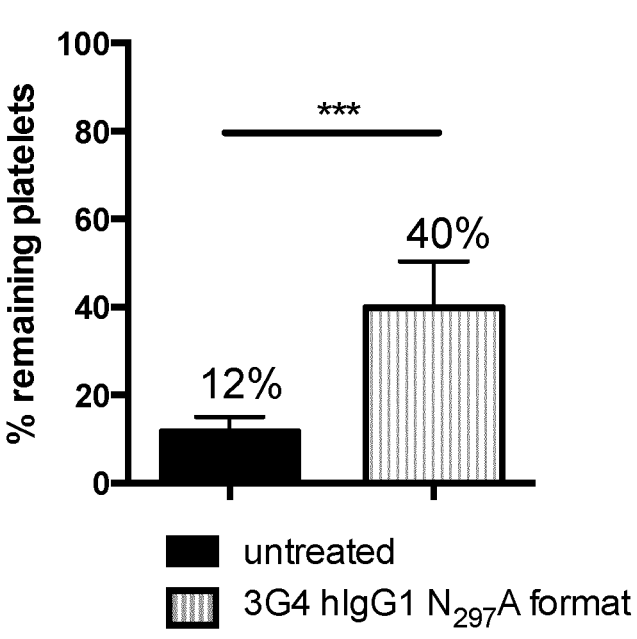
untreated
3G4 hIgG1 $N_{297}$A format

A

Figure 8:
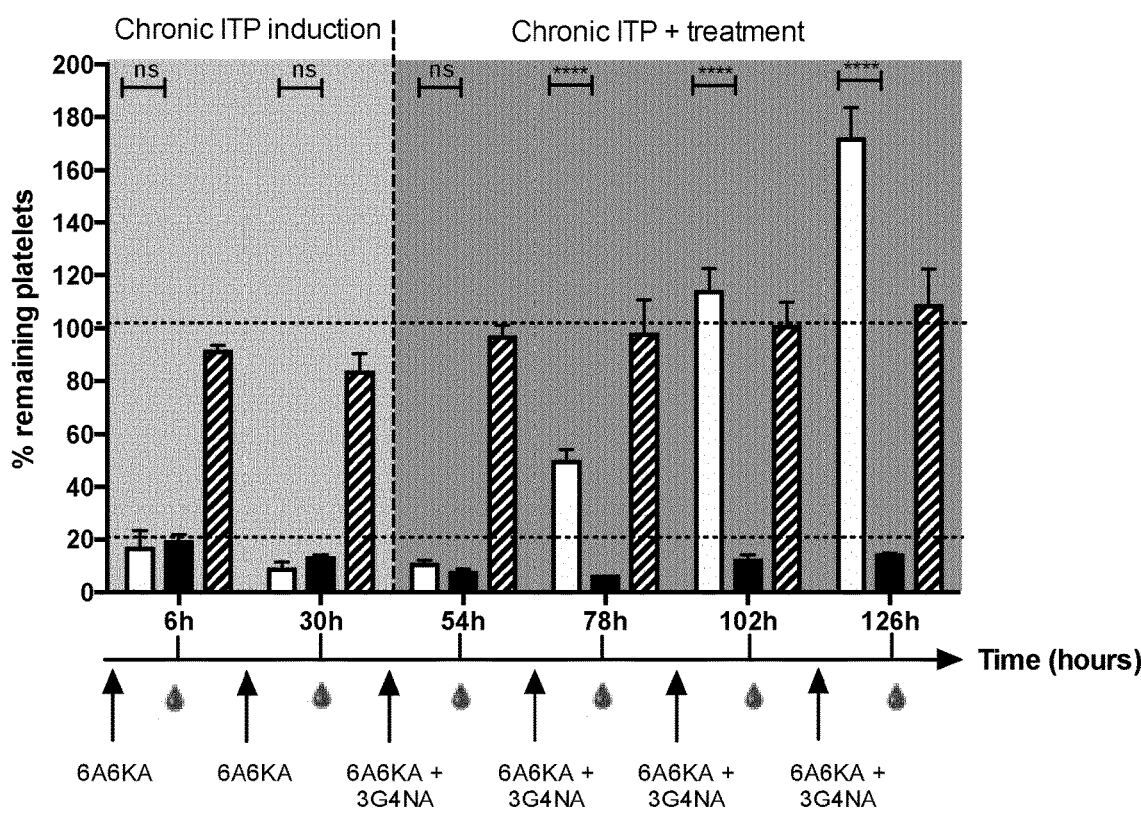

Figure 8 (continuation)
B
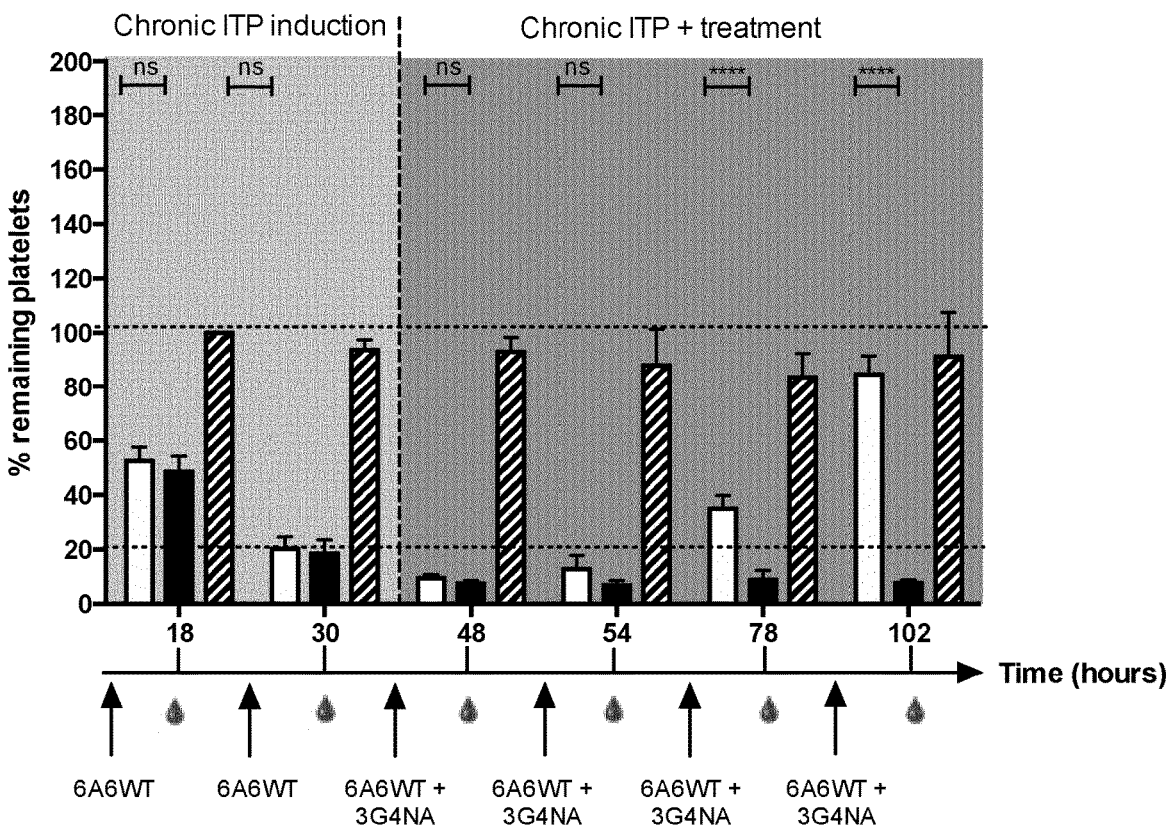
test group: 6A6WT+ 3G4 hIgG1 $N_{297}A$ format
control group1:  6A6WT + hIgG1 Hercept NA
control group2: hIgG1 Hercept WT

ANTIBODY BLOCKING HUMAN FCγRIIIA AND FCγRIIIB

CROSS-REFERENCE TO RELATED APPLICATIONS

This application is the U.S. National Stage of International Application PCT/EP2020/085495, filed Dec. 10, 2020, which claims the benefit of application Ser. No. 19/306,617.2, filed Dec. 10, 2019, all of which are hereby incorporated by reference.

REFERENCE TO SEQUENCE LISTING SUBMITTED ELECTRONICALLY

The instant application contains a Sequence Listing which has been submitted electronically in ASCII format and is hereby incorporated by reference in its entirety. Said ASCII copy, created on Nov. 30, 2022, is named 17783894_Sequence_listing.txt and is 30,183 bytes in size.

SUMMARY OF THE INVENTION

The present invention relates to novel antibodies, in particular murine monoclonal antibodies, chimeric and humanized, that are able to block specifically the human IgG receptors FcγRIIIA (CD16A) and FcγRIIIB (CD16B) as well as the amino and nucleic acid sequences coding for such antibodies. The invention also comprises the use of such antibodies or of fragments thereof as a medicament for the preventive and/or therapeutic treatment of diseases involving CD16, like autoimmune diseases, inflammatory disorders, allergies and infections, without inducing any adverse effects. In particular, these antibodies and fragments can prevent or treat anti-drug idiopathic thrombocytopenic purpura (ITP), rheumatoid arthritis (RA) and autoimmune hemolytic anemia (AIHA).

BACKGROUND OF THE INVENTION

Humans express several IgG receptors (FcγR or Fcgam-maR) that mediate the function of antibodies. Some of these FcγRs are activating receptors, responsible for the activation of the cells bearing them, leading to mediator release, endocytosis, phagocytosis, cytotoxic mechanisms and even enhancement of infection. These mechanisms can be triggered during pathology (autoimmunity, allergy, infection) but also following administration of therapeutic antibodies or drugs eliciting anti-drug antibody (ADA) responses. The activating FcγRs in humans are CD64 (FcγRI), CD32A (FcγRIIA), CD16A (or "FcγRIIIA") and CD16B (or "FcγRIIIB"). FcγRIIIA (CD16A) is mainly expressed on NK cells and monocytes/macrophages. It presents a very strong homology to FcγRIIIB (CD16B) that is mainly expressed, and at very high levels, on neutrophils.

Immune thrombocytopenia purpura (ITP) is one of the most common immunological disorders with moderate to severe symptoms and bleeding disorders (Kistangari et al, 2013). It relies on autoantibodies directed against platelet antigens leading to clearance of platelets from the periphery in the spleen and liver (Najean Y et al, 1997; Chong B H, 2009). Pathogenic IgG antibodies in ITP patients target mainly platelet surface glycoprotein antigens: GPIIb/IIIa (70-80% cases), GPIb/IX (20-40% cases) or both (Kistangari et al, 2013). Platelet opsonization by IgG antibodies leads to platelet engulfment and destruction by phagocytosis. Depending on the platelet antigen target, phagocytosis requires IgG receptors (FcγR) when anti-GPIIb/IIIa antibodies are involved, or requires hepatocyte Ashwell-Morell receptors when anti-GPIb antibodies are involved as the latter lead to platelet desialylation (Li J. et al, 2015). Severe ITP patients display platelet counts lower than $30\times10^9/L$ and are considered chronic if ITP lasts for >1 year. These patients are submitted to sequential lines of therapy to restore and maintain platelet counts at least over $30\times10^9/L$, but preferably over $50\text{-}80\times10^9/L$ (Portielje J E. Et al, 2001; Rodeghiero F. et al, 2009).

First-line therapy for ITP is typically glucocorticoids to decrease antibody production and platelet clearance. Second-line therapies include splenectomy with a 50-70% response rate resulting in durable remission, B cell depletion (anti-CD20 rituximab mainly) with 20% durable remission, and administration of thrombopoietin (TPO) mimetics with 60-80% response rates but probable lifelong administration (Chaturvedi S. et al, 2018).

Polymorphisms in the gene encoding CD16A (FcγRIIIA), a member of the human IgG receptor family (FcγR), are over-represented in ITP patients (Foster C B et al, 2001; Fujimoto T. T. et al, 2001 and Gillis C et al, 2014). The CD16A gene harbors a functional polymorphism at position 158, leading to a valine (V) or a phenylalanine (F) that increase or reduce, respectively, affinity of this receptor for IgG1, IgG2 and IgG3 (Bruhns P. et al, 2009). Thus, patients harboring a CD16A V/V polymorphism are expected to display increased opsonized-platelet clearance compared to those harboring F/F, or F/V polymorphisms. CD16A is expressed mainly on NK cells and subpopulations of mono-cytes and macrophages, whereas its closest homolog (97% amino acid homology), CD16B, essentially on neutrophils (Bruhns P. et al, 2015).

CD16A/CD16B-double transgenic mice infused with a mouse monoclonal antibody to the FcγRIII receptor family (mAb 3G8 targeting FcγRIIIA and FcγRIIIB cf. Fleit H B. et al, 1982) demonstrated severe reactions (Flaherty M M et al, 2012) that resemble IgG-mediated anaphylactic reactions (Finkelman F D et al. 2007; Gillis C M et al. 2015). In humans, therapeutic targeting of CD16A/FcγRIIIA in refractory ITP patients to increase the platelet count has been also attempted with the monoclonal antibody (mAb) 3G8 or with a humanized aglycosylated version thereof (GMA161). Mouse mAb 3G8 infusions led to increased platelet counts in the first case report (Clarkson S B et al, 1986) and in 50% patients of a follow-up study (Nakar C T. et al, 2009), but were accompanied by neutropenia, NK cell depletion, significant fever-chill-vomiting reactions and human anti-mouse antibody responses (HAMA). GMA161 infusions with the starting dose led also to increased platelet counts in 50% patients, but accompanied by dramatic, transient decrease in the white blood cell counts (Nakar C T. et al, 2009; Bussel J B et al, 2006). In view of these inacceptable side effects, trials with mAb 3G8 and GMA161 have since been stopped. These side effects are supposedly due to the property of mAb 3G8 or its humanized version GMA161 to aggregate CD16A or to aggregate CD16B on the cell surface, leading to the activation of the cells expressing these receptors.

In fact, as of today, no specific anti-CD16 blocking antibody devoid of side effects (i.e. a non-activating antibody) has been generated. There is thus still a need for novel antibodies specifically targeting and blocking CD16A and CD16B without activating the cells expressing these receptors, as these antibodies could be used for treating efficiently autoimmune diseases or other antibody-induced diseases.

DETAILED DESCRIPTION OF THE INVENTION

Antibodies of the Invention

The present inventors herein report the identification of a novel anti-human FcγRIII mAb (clone 3G4), with antagonistic properties and devoid of secondary reactions when injected in mice expressing all human FcγRs (FcγRI, FcγRIIA, FcγRIIB, FcγRIIIA, FcγRIIIB). The Complementary Determining Regions (CDRs) of this mAb were obtained by cloning and sequencing. They were used to generated a mouse-human chimeric antibody containing a human IgG1 heavy chain and a human kappa light chain (hereafter referred to as the chimeric antibody of the invention).

This chimeric antibody was further modified by introducing a N297A mutation in the human IgG1 heavy chain (termed herein 3G4NA) that results in a non-glycosylated format to restrict the interaction of the Fc domain with FcγRs. This aglycosylated mouse-human chimeric version (3G4NA) inhibited acute thrombocytopenia induction, and restored normal platelet counts in hFcγR$^{KI}$ mice suffering from severe chronic Immune Thrombocytopenia Purpura (ITP).

The 3G4NA monoclonal antibody represents a novel therapeutic solution in the prevention of several pathologies in which antibodies are pathogenic, as demonstrated below.

Here, the efficacy of 3G4NA has been demonstrated using in vivo models of acute and chronic autoimmune thrombocytopenia (platelet deficiency) using mice expressing the entire family of human FcγRs (FcγRI, FcγRIIA, FcγRIIB, FcγRIIIA and FcγRIIIB, generated by Regeneron Pharmaceuticals). Importantly, and contrary to the anti-CD16 antibodies of the prior art, no toxicity or adverse reactions has been observed after single or multiple administrations of this mAb to mice expressing all human FcγRs.

The 3G4 antibody of the invention (and its chimeric version and its chimeric modified version 3G4NA) is able to bind the extracellular domains of CD16A on monocytes, macrophages and NK cells, and the extracellular domains of CD16B on neutrophils, and inhibit their physical interaction with IgGs. Unlike the prior anti-CD16 antibodies such as mAb 3G8, this binding does 5 not induce intracellular signal events in said cells leading to cell activation. Instead, it blocks the cell activation. Therefore, this blocking (antagonistic) antibody is very useful to protect individuals from pathogenic effects of antibodies or of immune complexes. It can therefore be used in the prevention and/or in the treatment of diseases in which activation of the CD16A and/or CD16B should be prevented or reduced, notably in inflammatory responses such as those caused by auto-immune disorders.

In a first aspect, the present invention targets anti-CD16 antibodies or antigen-binding fragments thereof, that can specifically bind and antagonize FcγRIII receptors (CD16), more preferably FcγRIIIA and/or FcγRIIIB.

In other terms, the present inventions targets an antagonistic antibody or an antigen-binding fragment thereof that binds specifically to CD16.

The term "antibody" is used herein in the broadest sense and specifically covers monoclonal antibodies (including full length monoclonal antibodies) of any isotype such as IgG, IgM, IgA, IgD, and IgE, polyclonal antibodies, multispecific antibodies, chimeric antibodies, and antigen-binding fragments. An antibody reactive with a specific antigen can be generated by recombinant methods such as selection of libraries of recombinant antibodies in phage or similar vectors, or by immunizing an animal with the antigen or an antigen-encoding nucleic acid.

In a preferred embodiment, the antibodies of the invention are monoclonal IgGs.

A typical antibody is comprised of two identical light chains and two identical heavy chains that are joined by disulfide bonds. As used in the invention, the term "light chain" refers to mammalian immunoglobulin light chain, lambda (λ) or kappa (κ), having two successive domains: one constant domain and one variable domain. As used in the invention, the term "heavy chain" refers to chain of mammalian immunoglobulin denoted by: alpha (α), delta (δ), epsilon (ε), gamma (γ), and mu (μ). Each heavy chain has two regions, the constant region and the variable region. The constant region is identical in all antibodies of the same isotype. The variable region of each heavy chain is composed of a single Ig domain. The "variable region" or "variable domain" of an antibody refers to the amino-terminal domains of the heavy or light chain of the antibody. The variable domain of the heavy chain may be referred to as "V$_H$". The variable domain of the light chain may be referred to as "V$_L$". These domains are generally the most variable parts of an antibody and contain the antigen-binding sites. Each variable region contains three segments called "complementarity-determining regions" ("CDRs") or "hypervariable regions" ("HVRs"), which are primarily responsible for binding an epitope of an antigen and are interspersed with regions that are more conserved, designated "Framework Regions" (FR). The CDRs thus direct the specificity of the binding of the antibody. They are usually referred to as CDR1, CDR2, and CDR3, numbered sequentially from the N-terminus.

Each VH and VL is composed of three CDRs and four FRs, arranged from amino-terminus to carboxy-terminus in the following order: FR1, CDR1, FR2, CDR2, FR3, CDR3, FR4. The assignment of amino acid sequences to each domain is in accordance with well-known conventions (for example, the IMGT unique numbering convention as disclosed by Lefranc, M.-P., et al., Dev. Comp. Immunol., 27, 55-77 (2003)). The functional ability of the antibody to bind a particular antigen depends on the variable regions of each light/heavy chain pair, and is largely determined by the CDRs. The variable region of the heavy chain differs in antibodies produced by different B cells, but is the same for all antibodies produced by a single B cell or B cell clone (or hybridoma). By contrast, the constant regions of the antibodies mediate the binding of the immunoglobulin to host tissues or factors, including various cells of the immune system (e.g. effector cells) and the first component (Clq) of the classical complement system.

In a particular aspect, the antibodies and fragments of the invention comprise the heavy chain variable and constant regions encoded by the cDNA contained in the plasmids used to transform the E. coli cells which have been deposited at the CNCM (Collection Nationale de Cultures de Microorganismes) of Institut Pasteur on Nov. 25, 2019 under the name "pUC gamma1 mAb 3G4 heavy chain anti-human CD16", under the number CNCM 1-5459.

In another particular aspect, the antibodies and fragments of the invention comprise the light chain variable and constant regions encoded by the cDNA contained in the plasmids used to transform the E. coli cells which have been deposited at the CNCM (Collection Nationale de Cultures de Microorganismes) of Institut Pasteur on Nov. 25, 2019 under the name "pUC gamma1 mAb 3G4 light chain anti-human CD16", under the number CNCM 1-5458.

In a preferred embodiment, the antibodies and fragments of the invention comprise the light chain variable and constant regions encoded by the cDNA contained in the plasmids used to transform the *E. coli* cells deposited as CNCM 1-5458 and the heavy chain variable and constant regions encoded by the cDNA contained in the plasmids used to transform the *E. coli* cells deposited as CNCM 1-5459.

In a more preferred embodiment, the antibodies and fragments of the invention comprise the heavy chain variable and constant regions encoded by the cDNA contained in the plasmids used to transform the *E. coli* cells which have been deposited at the CNCM (Collection Nationale de Cultures de Microorganismes) of Institut Pasteur on Nov. 25, 2019 under the name "pUC gamma1 variant N297A mAb 3G4 heavy chain anti-human CD16", under the number CNCM I-5460.

In an even more preferred embodiment, the antibodies and fragments of the invention comprise the light chain variable and constant regions encoded by the cDNA contained in the plasmids used to transform the *E. coli* cells deposited as CNCM 1-5458 and the heavy chain variable and constant regions encoded by the cDNA contained in the plasmids used to transform the *E. coli* cells deposited as CNCM 1-5460.

In another particular aspect, the antibodies and fragments of the invention comprise:

a) a light chain comprising three CDRs of the sequences SEQ ID NO:1, 2 or 3, or having a sequence of at least 80%, preferably 85%, 90%, 95% and 98% identity with sequences SEQ ID NO:1, 2 or 3 after optimal alignment and b) a heavy chain comprising three CDRs of the sequences SEQ ID NO: 4, 5 or 6, or having a sequence of at least 80%, preferably 85%, 90%, 95% and 98% identity with sequences SEQ ID NO: 4, 5 or 6 after optimal alignment.

For ease of understanding, these CDR sequences are listed in Table 1:

TABLE 1

| amino acid sequences of SEQ ID NO: 1-6 | | |
|---|---|---|
| | SEQ ID NO : | Amino acid sequences |
| CDR1 $V_L$ | 1 | QDIIKN |
| CDR2 $V_L$ | 2 | YAT |
| CDR3 $V_L$ | 3 | LQFYEFPYT |
| CDR1 $V_H$ | 4 | GYTFIRNW |
| CDR2 $V_H$ | 5 | IDPSDGES |
| CDR3 $V_H$ | 6 | TRSRYYGGDWDWYFDV |

More precisely, the anti-CD16 antibodies of the invention or antigen-binding fragments thereof comprise a light chain comprising the CDR-L1, CDR-L2 and CDR-L3 having respectively the amino acid sequences SEQ ID NO: 1, 2 and 3; and a heavy chain comprising CDR-H1, CDR-H2 and CDR-H3 having respectively the amino acid sequences SEQ ID NO: 4, 5 and 6.

In one embodiment, the antibody of the invention, or antigen-binding fragment thereof, comprises:

a) a light chain variable domain ($V_L$) of sequence SEQ ID NO: 7, or an amino acid sequence having at least 80%, preferably 85%, 90%, 95% and 98% identity with SEQ ID NO: 7 after optimal alignment and b) a heavy chain variable domain ($V_H$) of sequence SEQ ID NO: 8, or an amino acid sequence having at least 80%, preferably 85%, 90%, 95% and 98% identity with SEQ ID NO:8 after optimal alignment.

By "optimal alignment with a preferred sequence", it is herein meant the two sequences have been aligned by means of a global alignment of the sequences in their entirety. This alignment is preferably performed by means of an algorithm that is well known by the skilled person, such as the one disclosed in Needleman and Wunsch (1970). Accordingly, sequence comparisons between two amino acid sequences or two nucleotide sequences can be performed for example by using any software known by the skilled person, such as the "needle" software using the "Gap open" parameter of 10, the "Gap extend" parameter of 0.5 and the "Blosum 62" matrix. Two sequences are "optimally aligned" when they are aligned so as to produce the maximum possible score for that pair of sequences, which might require the introduction of gaps in one or both of the sequences to achieve that maximum score. While optimal alignment and scoring can be accomplished manually, the process is facilitated by the use of a computer-implemented alignment algorithm, e.g., gapped BLAST 2.0, described in Altschul et al., (1997) Nucleic Acids Res. 25:3389-3402, and made available to the public at the National Center for Biotechnology Information website.

The invention also provides antibodies or fragments whose amino acid sequences are or contains sequences that are "similar" or "substantially similar" to SEQ ID NO:1 to SEQ ID NO:8. "Similarity" of two targeted amino acid sequences can be determined by calculating a similarity score for the two amino acid sequences. As used herein, the "similarity score" refers to the score generated for the two sequences using the BLOSUM62 amino acid substitution matrix, a gap existence penalty of 11, and a gap extension penalty of 1, when the two sequences are optimally aligned. Two amino acid sequences are substantially similar if their similarity score exceeds a certain threshold value. The threshold value can be any integer ranging from at least 1190 to the highest possible score for a particular reference sequence (e.g., SEQ ID NO:1-8). For example, the threshold similarity score can be 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, or higher. If in a particular embodiment of the invention, the threshold score is set at, for example, 1300, and the reference sequence is any of SEQ ID NO:1-8, then any amino acid sequence that can be optimally aligned with any of SEQ ID NO:1-8 to generate a similarity score of greater than 1300 is be held as "similar" to SEQ ID NO:1-8. Amino acid substitution matrices and their use in quantifying the similarity between two sequences are well-known in the art and described, e.g., in Dayhoff et al. (1978), and in Henikoff et al. (1992). To generate accurate similarity scores using NCBI BLAST, it is important to turn off any filtering, e.g., low complexity filtering, and to disable the use of composition based statistics. One should also confirm that the correct substitution matrix and gap penalties are used.

In a preferred embodiment, the antibody of the invention, or antigen-binding fragment thereof, comprises the light chain variable domain of SEQ ID NO:7 and the heavy chain variable domain of SEQ ID NO:8.

For ease of understanding, these CDR sequences are listed in Table 2:

TABLE 2

| amino acid sequences of SEQ ID NO: 7-8 | | |
|---|---|---|
| | SEQ ID NO: | Amino acid sequences |
| 3G4 light chain variable domain amino acid sequence | 7 | DIVLTQSPSSISASLGDRITITCQATQ DIIKNLNWYQQKPGKPPSFLIYYATEV AEGVPSRFSGSGSGSDYSLTISNLESE DFADYYCLQFYEFPYTFGGGTKLEIK |
| 3G4 heavy chain variable domain amino acid sequence | 8 | GVQLQESGAELVRPGSSVKLSCKPSGY TFIRNWIHWVKQRPIQGLEWIGAIDPS DGESHYNHKFTDKATLTVDKSSSTGYM QLNSLTSEDSAVYYCTRSRYYGGDWDW YFDVWGTGTTVTVSS |

In one embodiment, the present application relates to polyclonal antibodies. A "polyclonal antibody" is an antibody which was produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunized animal.

According to another embodiment, the antibody of the invention, or antigen-binding fragment thereof, is a monoclonal antibody, e.g., a murine monoclonal antibody, or an antigen-binding fragment thereof. As used herein, the term "monoclonal antibody" refers to an antibody arising from a nearly homogeneous antibody population. More particularly, the individual antibodies of a population are identical except for a few possible naturally-occurring mutations which can be found in minimal proportions. In other words, a monoclonal antibody consists of a homogeneous antibody population arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one class and subclass, and light chains of only one type. Monoclonal antibodies are highly specific and are directed against a single antigen. An "antigen" is a predetermined molecule to which an antibody can selectively bind. The target antigen may be a polypeptide, a carbohydrate, a nucleic acid, a lipid, a hapten or any other naturally occurring or synthetic compound. Preferably, the target antigen is a polypeptide.

An "epitope" is the site on the antigen to which an antibody specifically binds. It can be formed by contiguous residues or by non-contiguous residues brought into close proximity by the folding of an antigenic protein. Epitopes formed by contiguous amino acids are typically retained on exposure to denaturing solvents, whereas epitopes formed by non-contiguous amino acids are typically lost under said exposure.

In one embodiment, the invention provides antagonistic antibodies or antigen-binding fragments thereof capable of inhibiting the interaction of CD16 with its ligands. Specifically, the antibodies or antigen-binding fragments thereof of the invention are capable of inhibiting the interaction of IgGs with the CD16A and CD16B receptors, and their subsequent activation. In other words, the antibodies of the invention are capable of inhibiting CD16-mediated signalization induced by IgGs. They are therefore referred to as antagonistic antibodies—or "CD16 blocking antibodies".

Figure 2:
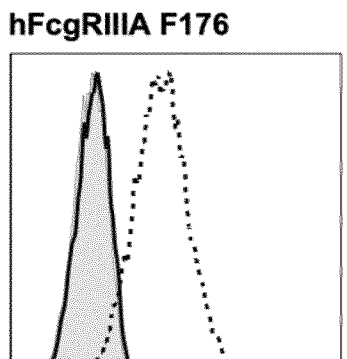
Figure 2:
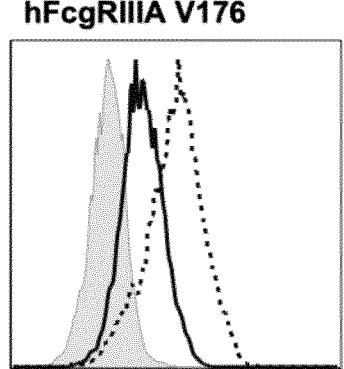
Figure 2:
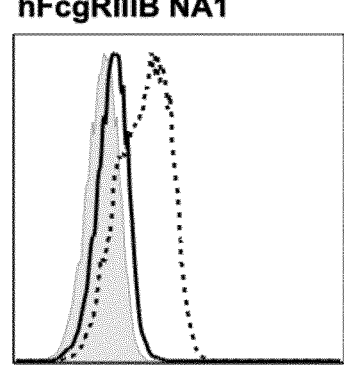
Figure 2:
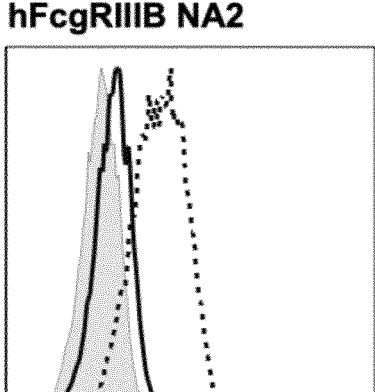
Figure 2:
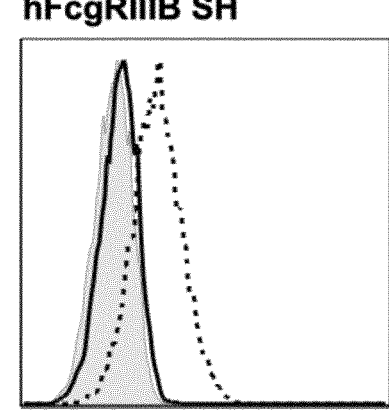

Preferably, the antibodies of the present application have a high affinity for CD16A and/or CD16B, in particular for all the polymorphic variants of CD16A (the higher affinity V158 variant and the lower-affinity F158 variant) and/or all the polymorphic variants of CD16B (NA1, NA2, SH variants) found in the human population (cf. FIG. 2). More preferably, they possess a very low dissociation constant with these receptors, in particular with CD16A V158 variant. For example, a low dissociation constant is inferior or equal to 50 nM and may reach down to the picomolar range ($10^{-12}$ M). More specifically, the antibodies of the invention or antigen-binding fragments thereof have a dissociation constant ($K_D$) with human CD16A V158 comprised between about 5 nM and about 20 nM as measured by Surface Plasmon Resonance (on a ProteON, Biorad). The inventors have indeed determined that the 3G4 mouse-human chimeric monoclonal antibody of the invention has a $K_D$ of about 7.9 nM for human CD16A V158 ectodomains of SEQ ID NO:18, whereas the modified 3G4 hIgG1 N297A has a $K_D$ of about 16 nM for human CD16A V158 ectodomains of SEQ ID NO:18. This affinity is within the same range as the prior art antibody 3G8 (see examples below).

As used herein, the term "$K_D$" refers to the dissociation constant of a particular antibody/antigen interaction. As used herein the term "binding affinity" or "affinity of binding" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

Another characteristic of the anti-CD16 antibodies of the invention is their ability to completely inhibit the activation of CD16A and CD16B by immunoglobulins ("non-activating activity" or "antagonistic activity" or "blocking activity"). Assays for measuring ability of an antibody to block the activation of CD16A and CD16B are known. For example, they rely on the detection of calcium mobilization in peripheral blood NK cells, or calcein-release assay to detect cell lysis using freshly isolated NK cells (see e.g., WO 2006/125668 and WO 2007/009065). Commercially available ADCC assays can also be used.

More generally, the anti-CD16 antibodies of the invention are not capable of triggering cell killing, after their binding to the cells expressing CD16A or CD16B. Their effect is therefore opposite to the other anti-CD16A antibodies of the prior art (e.g., those disclosed in WO 2006/125668).

Examples of expression vectors useful for expression of CD16A and other polypeptides for use in blocking/binding assays include mammalian expression vectors (e.g., pCDNA 3.1 or pCI-neo) that contain a strong promoter/enhancer sequence (e.g., CMV immediate early) and a polyadenylation/transcription termination site flanking a poly-linker region into which the CD16A gene or CD16B is introduced. Usually the vector includes a selectable marker such as a neomycin resistance gene. In one embodiment, the CD16A expressed for use in blocking assays has the sequence SEQ ID NO: 17 (F158) or SEQ ID NO: 18 (V158). Additional CD16A variants and substitutes will be known to, or readily discernible from the scientific literature by, the ordinarily skilled artisan.

It must be understood here that the invention preferably does not relate to antibodies in natural form, i.e., they are not taken from their natural environment but are isolated or obtained by purification from natural sources or obtained by genetic recombination or chemical synthesis and thus they can carry "unnatural" amino acids as will be described below. They can also be multispecific, for example TandAb or Flexibody.

In another aspect, the invention relates to chimeric or humanized antibodies, or antigen-binding fragments, which can be obtained by genetic engineering or by chemical synthesis.

Specifically, the anti-CD16 antibodies of the invention are chimeric antibodies.

The term "chimeric antibody" as used herein refers to an antibody containing a natural variable region (light chain and heavy chain) derived from an antibody of a given species in combination with constant regions of the light chain and of the heavy chain of an antibody of a species heterologous to said given species. Thus, a "chimeric antibody", as used herein, is an antibody in which the constant region, or a portion thereof, is altered, replaced, or exchanged, so that the variable region is linked to a constant region of a different species, or belonging to another antibody class or subclass. "Chimeric antibody" also refers to an antibody in which the variable region, or a portion thereof, is altered, replaced, or exchanged, so that the constant region is linked to a variable region of a different species, or belonging to another antibody class or subclass. Such chimeric antibodies, or fragments of same, can be prepared by recombinant engineering. For example, the chimeric antibody could be produced by cloning recombinant DNA containing a promoter and a sequence coding for the variable region of a non-human monoclonal antibody of the invention, notably murine, and a sequence coding for the human antibody constant region. A chimeric antibody according to the invention coded by one such recombinant gene could be, for example, a mouse-human chimera, the specificity of this antibody being determined by the variable region derived from the murine DNA and its isotype determined by the constant region derived from human DNA.

In a preferred embodiment, the present invention relates to a chimeric antibody, or an antigen binding fragment thereof, comprising a light chain variable domain ($V_L$) comprising CDR-L1, CDR-L2 and CDR-L3 having respectively the amino acid sequence SEQ ID NO: 1, 2 and 3; and a heavy chain variable domain ($V_H$) comprising CDR-H1, CDR-H2 and CDR-H3 having respectively the amino acid sequence SEQ ID NO: 4, 5 and 6.

In another embodiment, the present invention relates to a chimeric antibody, or an antigen-binding fragment thereof, comprising a light chain variable domain ($V_L$) comprising the amino acid sequence SEQ ID NO: 7 and a heavy chain variable domain ($V_H$) comprising the amino acid sequence SEQ ID NO: 8.

In a specific embodiment, the present invention relates to a chimeric antibody, or an 5 antigen-binding fragment thereof, comprising a light chain variable domain ($V_L$) of sequence SEQ ID NO: 7 and a heavy chain variable domain ($V_H$) of sequence SEQ ID NO: 8.

In another aspect, the present invention provides humanized antagonistic anti-CD16 antibodies, or antigen-binding fragments thereof.

As used herein, the term "humanized antibody" refers to a chimeric antibody which contain minimal sequence derived from non-human immunoglobulin. In one embodiment, a humanized antibody is a human immunoglobulin (recipient antibody) in which residues from a CDR of the recipient are replaced by residues from a CDR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the Heavy (H) chain, and in the Light (L) chain, no more than 3. The humanized antibody optionally will also comprise at least a portion of an immunoglobulin constant region (Fc), typically that of a human immunoglobulin.

The goal of humanization is a reduction in the immunogenicity of a xenogenic antibody, such as a murine antibody, for introduction into a human, while maintaining the full antigen binding affinity and specificity of the antibody. Humanized antibodies, or antibodies adapted for non-rejection by other mammals, may be produced using several technologies such as resurfacing and CDR grafting. As used herein, the resurfacing technology uses a combination of molecular modeling, statistical analysis and mutagenesis to alter the non-CDR surfaces of antibody variable regions to resemble the surfaces of known antibodies of the target host.

Strategies and methods for the resurfacing of antibodies, and other methods for reducing immunogenicity of antibodies within a different host, are disclosed in U.S. Pat. No. 5,639,641, which is hereby incorporated in its entirety by reference. Briefly, in a preferred method, (1) position alignments of a pool of antibody heavy and light chain variable regions is generated to give a set of heavy and light chain variable region framework surface exposed positions wherein the alignment positions for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5 angstroms (Å) of any atom of any residue of the complementarity-determining regions of the rodent antibody; and (5) the humanized rodent antibody having binding specificity is produced. Antibodies can be humanized using a variety of other techniques including CDR-grafting (EP 0 239 400; WO 91/09967; U.S. Pat. Nos. 5,530,101; and 5,585,089), veneering or resurfacing (EP 0 592 106; EP 0 519 596), and chain shuffling (U.S. Pat. No. 5,565,332). Human antibodies can be made by a variety of methods known in the art including phage display methods (U.S. Pat. Nos. 4,444,887, 4,716,111, 5,545,806, and 5,814,318).

Another technique which may be employed either as an alternative, or in addition, to the methods described above for reducing immunogenicity, is the "deimmunisation". Deimmunisation technology involves the identification and removal of T helper (Th) cell epitopes from antibody and other protein biological therapeutic agents. Th cell epitopes comprise short peptide sequences within proteins that have the capacity to bind to MHC class II molecules. The peptide-MHC class II complexes can be recognized by T cells and can trigger the activation and differentiation of Th cells, which is required to initiate and sustain immunogenicity through interaction with B cells, thus resulting in the secretion of antibodies that bind specifically to the administered biological therapeutic agent. For antibody deimmunisation, the Th-cell epitopes are identified within the antibody sequence, for example by a computer-based method for predicting the binding of peptides to human MHC class II molecules. To avoid recognition by T cells, the Th cell epitopes thus identified are eliminated from the protein sequence by amino acid substitutions. This may be achieved through the use of standard molecular biology techniques, such as for example site-directed mutagenesis to alter the nucleic acid sequence encoding the Th cell epitope in the therapeutic protein. In this way, an antibody or antigen-binding fragment may be modified so that HAMA (Human anti mouse antigenic) and/or anti-idiotypic response(s) are reduced or avoided. Thus, in specific embodiments, the antibodies of the invention have been modified to remove any Th cell epitopes present in their sequence. Such binding molecules are referred to herein as deimmunised antibodies.

The humanized antibodies of the invention arise from the murine antibody described above.

More particularly, the invention relates to a humanized antibody, or antigen-binding fragments thereof, comprising a light chain variable domain comprising CDR-L1, CDR-L2 and CDR-L3 having respectively the amino acid sequence SEQ ID NO. 1, 2 and 3; and a heavy chain variable domain comprising CDR-H1, CDR-H2 and CDR-H3 having respectively the amino acid sequence SEQ ID NO: 4, 5 and 6.

Thus, in a specific embodiment, the present invention provides humanized antibodies or antigen-binding fragments thereof which specifically bind CD16A and CD16B and inhibit the interaction between these receptors and their ligands (IgGs) and subsequent signaling.

In another specific embodiment, the antagonistic antibody or antigen-binding fragment of the invention is fully human. The term "fully human" as used herein relates to an antibody or antigen-binding fragment whose amino acid sequences are derived from (i.e. originate or may be found in) humans. Preferably, it is a full-human antibody comprising a light chain comprising the CDR-L1, CDR-L2 and CDR-L3 having respectively the amino acid sequences SEQ ID NO: 1, 2 and 3; and a heavy chain comprising CDR-H1, CDR-H2 and CDR-H3 having respectively the amino acid sequences SEQ ID NO: 4, 5 and 6.

Antibody Fragments of the Invention

An "antibody fragment" comprises a portion of an intact antibody, preferably the antigen binding and/or the variable region of the intact antibody. Examples of antibody fragments include Fab, Fab', $F(ab')_2$ and Fv fragments; diabodies; linear antibodies (see U.S. Pat. No. 5,641,870); single-chain antibody molecules and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments having different antigen-binding activity and is still capable of cross-5 linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known. The term "Fv" as used herein refers to the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three hyper variable regions specific for an antigen) has the ability to recognize and bind antigen, although at a lower affinity than the entire binding site. "Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding.

In a preferred embodiment, the antibody or fragment of the invention is multispecific, and in particular bispecific. As such, it can be chosen in the group consisting of: bispecific IgGs, IgG-scFv$_2$, (scFv)$_4$-IgG, (Fab')$_2$, (scFv)$_2$, (dsFv)$_2$, Fab-scFv fusion proteins, (Fab-scFv)$_2$, (scFv)$_2$-Fab, (scFv-$C_H2$-$C_H3$-scFv)$_2$, bibody, tribody, bispecific diabody, disulfide-stabilized (ds) diabody, 'knob-into whole' diabody, single-chain diabody (scDb), tandem diabody (TandAb), flexibody, DiBi miniantibody, [(scFv)$_2$-Fc]$_2$, (scDb-$C_H3$)2, (scDb-Fc)$_2$, Di-diabody, Tandemab., etc.

"Functional fragments" of the antibodies of the invention comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

As used therein, the term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "cross-over" sFv fragments in which the $V_H$ and $V_L$ domains of the two antibodies are present on different polypeptide chains. Diabodies are described in greater detail in, for example, EP 404,097; WO 93/11161.

More particularly, the invention provides an anti-CD16 functional fragment selected among the antibody fragments Fv, Fab, (Fab')$_2$, Fab', scFv, scFv-Fc and diabodies, or any fragment whose half-life has been increased by chemical modification.

The chemical modification as cited above, may be such as the addition of polyalkylene glycol such as polyethylene glycol (PEGylation) (PEGylated fragments are referred to as Fv-PEG, scFv-PEG, Fab-PEG, F(ab')$_2$-PEG and Fab'-PEG), or by incorporation in a liposome, microspheres or Poly (D, L-lactic-co-glycolic acid) (PLGA), said fragments possessing at least six of CDRs of the invention which is notably capable of exerting in a general manner activity, even partial, of the antibody from which it arises.

Preferably, said antigen-binding fragment will comprise or include a partial sequence of the variable heavy or light chain of the antibody from which they are derived, said partial sequence being sufficient to retain the same binding specificity as the antibody from which it arises and sufficient affinity, preferably at least equal to 1/100, more preferably at least 1/10 of that of the antibody from which it arises.

Preferably, this antigen-binding fragment will be of the types Fv, scFv, Fab, F(ab')$_2$, F(ab'), scFv-Fc or diabodies, which generally have the same binding specificity as the antibody from which they result.

According to the present invention, antigen-binding fragments of the invention can be obtained from the antibodies described above by methods such as enzyme digestion, including pepsin or papain, and/or by cleavage of the disulfide bridges by chemical reduction. The antigens-binding fragments can be also obtained by recombinant genetics techniques also known to a person skilled in the art or by peptide synthesis by means, for example, of automatic peptide synthesizers such as those sold by Applied BioSystems, etc.

In Vitro Use of the Antibodies and Fragments of the Invention

In another aspect, the antibodies or fragments of the invention may be conjugated to a labeling molecule, or a toxin. Where the labeling molecule or toxin is a protein, conjugation to the antibodies or fragments may occur through a peptide bond or through chemical conjugation. Thus antibodies or fragments according to the invention may be in the form of a fusion protein where the labeling molecule or toxin is linked to the antibodies or fragments by a peptide bond, preferably by a peptide linker, or it may be in the form of a chemical conjugate. For the avoidance of doubt, the term conjugation is used herein to mean that two components are physically linked together via a chemical bond, which includes a peptide bond (thus conjugates include fusion proteins), ester linkage, or disulphide bridge.

Conjugation of antibodies or fragments of the invention to a labeling molecule, such as a radiolabel or a fluorescent or luminescent (including chemiluminescent) label allows the binding molecule to be used as an immunological staining reagent. Such a reagent may be used in detecting, for example, tissue-infiltrating NK cells, monocytes, macrophages or neutrophils expressing FcγRIIIA or FcγRIIIB, or, where the binding molecule exhibits specificity for an additional antigen, in detecting NK-cell-binding molecule-additional antigen complexes. Detection of the latter may be particularly useful in the diagnosis of disease or in the monitoring of disease progression or remission.

In a particular aspect, the antibodies or fragments of the invention can be used in vitro as a reagent to stain cells expressing CD16A or CD16B in a biological sample. Where said antibodies or fragments have specificity for at least one further antigen, it may be used as the reagent by which the CD16A or CD16B-expressing cell-binding molecule-antigen complex can be identified. The antibodies or fragments of the invention may also be used to analyze and type patient samples ex vivo, as a biomarker, and to isolate CD16-expressing cells for ex-vivo therapy.

A "biological sample" may be any sample that may be taken from a subject. Such a sample must allow for the determination of the presence of CD16A or CD16B. The nature of the sample will thus be dependent upon the nature of the disorder. Preferred biological samples include samples such as a blood sample or a lymph sample (that contain macrophages, neutrophils and NK cells).

In particular, said biological sample can be obtained in a patient suffering from a "liquid tumor", i.e. a tumor of the blood or bone marrow such as leukemia and multiple myeloma. The "biological sample" as used herein also includes a solid cancer sample of the patient to be tested, when the disorder is a solid cancer. Such solid cancer sample allows the skilled person to perform any type of measurement of the level of the biomarker of the invention. In some cases, the methods according to the invention may further comprise a preliminary step of taking a solid cancer sample from the patient. By a "solid cancer sample", it is referred to a tumor tissue sample. Even in a cancerous patient, the tissue which is the site of the tumor still comprises non tumor healthy tissue. The "cancer sample" should thus be limited to tumor tissue taken from the patient. Said "cancer sample" may be a biopsy sample or a sample taken from a surgical resection therapy.

In one embodiment, the anti-CD16 antibodies or fragments of the invention are used to determine the level of CD16A or CD16B in a tissue or in cells derived from the tissue. In a preferred embodiment, the tissue is a diseased tissue. In a preferred embodiment of the method, the tissue is a tumor or a biopsy thereof. In a preferred embodiment of the method, a tissue or a biopsy thereof is first excised from a patient, and the levels of CD16 in the tissue or biopsy can then be determined in an immunoassay with the antibodies or antibody fragments of the invention.

In one aspect the present invention comprises a method of detecting in vitro the presence and/or the location of CD16 in a subject, said method comprising the steps of:

a) contacting a sample of said subject with an antibody or antigen-binding fragments thereof as described above; and (b) detecting the binding of said antibody with the sample.

The ability to use the anti-CD16 antibodies to detect CD16 in a biological sample in vitro or in vivo is advantageous for diagnosing the presence of a CD16-related disorder in a patient. The above-described method can be used to diagnose a CD16-related disorder in a patient, wherein the level of CD16 measured in said patient is compared with that of a normal reference subject or standard.

As used herein, "diagnosis" or "identifying a subject having" refers to a process of determining if an individual is afflicted with a disease or ailment (e.g., a CD16-related disorder). A CD16-related disorder is diagnosed for example by detecting an abnormal mutation or a significatively altered membrane expression level of the CD16 peptide in a biological sample of a patient in vitro or in vivo (see e.g., in Gillis C M et al, 2017 or in Breunis W B et al, 2009).

The present invention further provides labeled monoclonal antibodies, humanized antibodies and epitope-binding fragments thereof, for use in research or diagnostic applications. In a further preferred embodiment, the label is a radiolabel, a fluorophore, a chromophore, an imaging agent or a metal ion.

A method for diagnosis is also provided in which said labeled antibodies or epitope-binding fragments thereof are administered to a subject suspected of having a CD16-related disorder, and the distribution of the label within the body of the subject is measured or monitored.

For these applications, the invention encompasses a kit comprising antibodies or fragments as described hereinbefore and means for detecting said antibodies or fragments when bound to FcγRIIIA or FcγRIIIB. If the antibody or fragment is radiolabeled or labelled with a chemiluminescent label, the detection means may comprise film sensitive to the radio- or chemi-luminescent label. If the antibody or fragment is tagged with a histidine or c-myc tag, the kit may comprise an antibody which recognizes that tag.

Antibody Conjugates

In another aspect, the antibodies or fragments of the invention comprise a further functional domain. This further functional domain may be an enzyme that is capable of converting a pro-drug to an active drug. In this way binding molecules of the invention may be used in antibody-dependent enzyme pro-drug therapy (ADEPT).

If the antibody or fragment of the invention is conjugated to a toxin molecule, such as a ribosyl transferase, serine protease, guanyl cyclase activator, calmodulin-dependent adenyl cyclase, ribonuclease, DNA alkylating agent or mitosis inhibitor (e.g. doxorubicin) and the like, it may be used to target and kill NK cells and macrophages in humans. Such antibody or fragment may thus be used as an immunosuppressive agent. The skilled man will appreciate that as an alternative to being tagged with a labeling molecule or toxin via chemical conjugation, peptide labels or peptide toxins may also be used. For example, the antibody or fragment of the invention may be expressed as a fusion protein with an N- or C-terminal peptide tag such as a tetra- penta- or hexa-histidine tag, a c-myc tag or the like.

In a further embodiment, said further functional domain is a protein or peptide that confers an increased serum half-life on the binding molecule. An example of such a protein is serum albumin or the Fc portion of IgG, which may increase serum half-life of the binding molecule by virtue of its ability to bind to FcRn (the neonatal Fc receptor).

Preferred Mutations in the Fc Domain

It is also possible to increase the half-life of the antibodies of the invention by modifying the antibody amino acid sequence itself.

For example, the half-life of the antibodies or fragments of the invention can be increased by introducing the following amino acid mutations:

M252Y/S254T/T256E ("YTE"): this mutation increases the binding of the IgG or Fc domains to the IgG recycling receptor, FcRn, leading to a prolonged half-life (Dall'Acqua W F et al. 2002).

M428L/N434S ("LS"): this mutation increases the binding of the IgG or Fc domains to the IgG recycling receptor, FcRn, leading to a prolonged half-life (Zalevsky J et al, 2010).

L309D/Q311H/N434S ("DHS"): this mutation increases the binding of the IgG or Fc domains to the IgG recycling receptor, FcRn, leading to a prolonged half-life (Lee C H et al, 2019)

T307A/E380A/N434A: this mutation increases the binding of the IgG or Fc domains to the IgG recycling receptor, FcRn, leading to a prolonged half-life (Shields R L, et al. 2001).

Moreover, as the antibodies and fragments of the invention are intended to be used in the treatment and/or therapy in humans, their potential immunogenicity and deleterious effects should be minimized by any means.

It is therefore recommended to modify the Fc regions of these antibodies in order to abolish their effector functions, as already proposed in the art. In particular, it is better to mutate the Fc region of the antibodies in order to avoid the activation not only of the receptors FcγR (FcγRI, FcγRII, FcγRIII, FcγRIIIA, FcγRIIIB, Fcγn) but also of the C1q component of the complement, which plays important roles in opsonization, lysis of cell pathogens, and inflammatory responses.

As used herein, the term "Fc region" is used to define a C-terminal region of an IgG heavy chain. Although the boundaries may vary slightly, the human IgG heavy chain Fc region is defined to stretch from Cys226 to the carboxy terminus. The Fc region of an IgG comprises two constant domains, CH2 and CH3. The CH2 domain of a human IgG Fc region usually extends from amino acids 231 to amino acid 341. The CH3 domain of a human IgG Fc region usually extends from amino acids 342 to 447. The CH2 domain of a human IgG Fc region usually extends from amino acid 231-340. The CH2 domain is unique in that it is not closely paired with another domain. Rather, two N-linked branched carbohydrate chains are interposed between the two CH2 domains of an intact native IgG.

As used herein, an Fc region that "lacks effector function" does not bind the Fc receptor and/or does not bind the C1q component of complement nor trigger the biological responses characteristic of such binding.

It is possible to impair the effector function of antibodies by generating Fc regions that are not glycosylated (or "aglycosylated") at its usual glycosylation sites.

The term "glycosylation site" refers to an amino acid residue that is recognized by a mammalian cell as a location for the attachment of sugar residues. Amino acid residues to which carbohydrates, such as oligosaccharides, are attached are usually asparagine (N-linkage), serine (O-linkage), and threonine (O-linkage) residues. The specific sites of attachment usually have a characteristic sequence of amino acids, referred to as a "glycosylation site sequence." The glycosylation site sequence for N-linked glycosylation is: -Asn-X-Ser- or -Asn-X-Thr-, where X can be any of the conventional amino acids, other than proline. The Fc region of human IgG has two glycosylation sites, one in each of the CH2 domains. The glycosylation that occurs at the glycosylation site in the CH2 domain of human IgG is N-linked glycosylation at the asparagine at position 297 (Asn 297).

All the mutations proposed for the 3G8 antibody in WO 2007/009065 are herewith encompassed (cf., in particular, [0101] to [0110] and [0116] to [0122]).

In particular, it is possible to modify the Fc regions of the antibodies of the invention by mutating them with any of the following mutations:

N297A: this mutation replaces the asparagine able to receive N-glycosylation. This N-glycosylation is necessary for the interaction between the Fc region of IgG and human low-affinity FcγR (CD32A, CD32B, CD32C, CD16A, CD16B). It does not affect the interaction of IgG with the high-affinity FcγR, FcγRI/CD64.

N297D: similar mutation to N297A with same consequences on FcγR binding.

L234A, L235A (LALA): this double mutation abolishes the interaction between the Fc region of IgG and human low-affinity FcγR (CD32A, CD32B, CD32C, CD16A, CD16B). It does not affect the interaction of IgG with the high-affinity FcγR, FcγRI/CD64.

L234A, L235A, P329G (LALAPG): this triple mutation abolishes the interaction between the Fc region of IgG and all human FcγR, whether low-affinity FcγR (CD32A, CD32B, CD32C, CD16A, CD16B) or high-affinity FcγR (CD64).

Any of this mutation can be used to generate an efficient therapeutic antibody that can be safely administered to human beings.

Moreover, all the mutations known in the art to enhance the efficiency and reduce the adverse side effects of therapeutic antibodies are herewith encompassed.

Polynucleotide Encoding the Antibodies of the Invention

In a preferred embodiment, the antibody of the invention, under its chimeric, humanized or full-human form, has been recombinantly modified by introducing a N297A mutation in the human IgG1 heavy chain.

Another aspect of the present invention relates to an isolated nucleic acid characterized in that it is selected among the following nucleic acids (including any degenerate genetic code):

a) a nucleic acid sequence, DNA or RNA, coding for an antibody, or one of its functional fragments or derivatives, according to the invention;

b) a nucleic acid comprising a DNA sequence selected from the group of sequences consisting of SEQ ID NO 9 and 13 (encoding the light chains of the antibody of the invention);

c) a nucleic acid comprising a DNA sequence selected from the group of sequences consisting of SEQ ID NO. 10, 14 and 16 (encoding the heavy chains of the antibody of the invention);

d) a nucleic acid contained in the *E. coli* cells deposited at the Collection Nationale de Cultures de Microorganismes from Institut Pasteur, on Nov. 25, 2019, under the number 1-5458, 1-5459, or 1-5460; in particular a nucleic acid encoding the fragments of the invention, present in the pUC plasmids contained in said bacterial cells, or e) a nucleic acid whose sequence exhibits a percentage identity of at least 80%, preferably 85%, 90%, 95% and 98%, after optimal alignment with any of the sequence referred to in b) and c).

In a specific embodiment, the invention is directed to a pair of polynucleotides of the invention, wherein one of the polynucleotides encodes the heavy chain and the other polynucleotide encodes the light chain of an antibody of the invention.

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, defining a fragment or a region of a nucleic acid, containing unnatural nucleotides or not, and being either a double-strand DNA, a single-strand DNA or transcription products of said DNAs.

It should also be included here that the present invention does not relate to nucleotide sequences in their natural chromosomal environment, i.e., in a natural state. The sequences of the present invention have been isolated and/or purified, i.e., they were sampled directly or indirectly, for example by a copy, their environment having been at least partially modified. Isolated nucleic acids obtained by recombinant genetics, by means, for example, of host cells, or obtained by chemical synthesis should also be mentioned here.

"Nucleic sequences exhibiting a percentage identity of at least 80%, preferably 85%, 90%, 95% and 98%, after optimal alignment with a preferred sequence" means nucleic sequences exhibiting, with respect to the reference nucleic sequence, certain modifications such as, in particular, a deletion, a truncation, an extension, a chimeric fusion and/or a substitution, notably punctual. Preferably, these are sequences which code for the same amino acid sequences as the reference sequence, this being related to the degeneration of the genetic code, or complementarity sequences that are likely to hybridize specifically with the reference sequences, preferably under highly stringent conditions, notably those defined below. Hybridization under highly stringent conditions means that conditions related to temperature and ionic strength are selected in such a way that they allow hybridization to be maintained between two complementarity DNA fragments. On a purely illustrative basis, the highly stringent conditions of the hybridization step for the purpose of defining the polynucleotide fragments described above are advantageously as follows. DNA-DNA or DNA-RNA hybridization is carried out in two steps: (1) prehybridization at 42° C. for three hours in phosphate buffer (20 mM, pH 7.5) containing 5×SSC (1×SSC corresponds to a solution of 0.15 M NaCl+0.015 M sodium citrate), 50% formamide, 7% sodium dodecyl sulfate (SDS), 10×Denhardt's, 5% dextran sulfate and 1% salmon sperm DNA; (2) primary hybridization for 20 hours at a temperature depending on the length of the probe (i.e.: 42° C. for a probe >100 nucleotides in length) followed by two 20-minute washings at 20° C. in 2×SSC+2% SDS, one 20-minute washing at 20° C. in 0.1×SSC+0.1% SDS. The last washing is carried out in 0.1×SSC+0.1% SDS for 30 minutes at 60° C. for a probe >100 nucleotides in length. The highly stringent hybridization conditions described above for a polynucleotide of defined size can be adapted by a person skilled in the art for longer or shorter oligonucleotides, according to the procedures described in Sambrook, et al. (Molecular cloning: a laboratory manual, Cold Spring Harbor Laboratory; 3rd edition, 2001).

According to the invention, a variety of expression systems may be used to express the IgG antibody or fragment of the invention. In one aspect, such expression systems represent vehicles by which the coding sequences of interest may be produced and subsequently purified, but also represent cells which may, when transiently transfected with the appropriate nucleotide coding sequences, express an IgG antibody or fragment of the invention in situ.

The invention provides vectors comprising the polynucleotides of the invention. In one embodiment, the vector contains a polynucleotide encoding a heavy chain of the modified anti-CD16 antibody of the invention which carries a mutation in the Fc domain. In another embodiment, said polynucleotide encodes the light chain of the antibody of the invention. The invention also provides vectors comprising polynucleotide molecules encoding fusion proteins, modified antibodies, antibody fragments, and probes thereof.

In order to express the heavy and/or light chain of the anti-CD16 antibody of the invention, the polynucleotides encoding said heavy and/or light chains are inserted into expression vectors such that the genes are operatively linked to transcriptional and translational sequences.

"Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

Certain vectors are capable of directing the expression of genes to which they are operatively linked. Such vectors are referred to herein as "recombinant expression vectors" (or simply, "expression vectors"). In general, expression vectors of utility in recombinant DNA techniques are in the form of plasmids. In the present specification, "plasmid" and "vector" may be used interchangeably as the plasmid is the most commonly used form of vector. However, the invention is intended to include such forms of expression vectors, such as bacterial plasmids, YACs, cosmids, retrovirus, EBV-derived episomes, and all the other vectors that the skilled man will know to be convenient for ensuring the expression of the heavy and/or light chains of the antibodies of the invention. The skilled man will realize that the polynucleotides encoding the heavy and the light chains can be cloned into different vectors or in the same vector. In a preferred embodiment, said polynucleotides are cloned into two vectors.

Antibody Production and Host Cells

Polynucleotides of the invention and vectors comprising these molecules can also be used in vitro for the transformation of a suitable host cell which is also encompassed by the present invention. The term "host cell", as used herein, is intended to refer to a cell into which a recombinant expression vector has been introduced in order to express the antibody or fragment of the invention, or a part thereof.

These host cells are for example any cells containing at least one of the plasmid contained in the following deposited cells:

the E. coli cells which have been deposited at the CNCM (Collection Nationale de Cultures de Microorganismes) of Institut Pasteur on Nov. 25, 2019 under the name "pUC gamma1 mAb 3G4 heavy chain anti-human CD16", under the number CNCM 1-5459.

the E. coli cells which have been deposited at the CNCM (Collection Nationale de Cultures de Microorganismes) of Institut Pasteur on Nov. 25, 2019 under the name "pUC gamma1 mAb 3G4 light chain anti-human CD16", under the number CNCM 1-5458, or the E. coli cells which have been deposited at the CNCM (Collection Nationale de Cultures de Microorganismes) of Institut Pasteur on Nov. 25, 2019 under the name "pUC gamma1 variant N297A mAb 3G4 heavy chain anti-human CD16", under the number CNCM 1-5460.

It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein.

The present invention also encompasses cells into which a recombinant expression vector has been introduced in order to store, replicate and extract the recombinant expression vector. For example, these cells are:

the E. coli cells which have been deposited at the CNCM (Collection Nationale de Cultures de Microorganismes) of Institut Pasteur on Nov. 25, 2019 under the name "pUC gamma1 mAb 3G4 heavy chain anti-human CD16", under the number CNCM 1-5459.

the E. coli cells which have been deposited at the CNCM (Collection Nationale de Cultures de Microorganismes) of Institut Pasteur on Nov. 25, 2019 under the name "pUC gamma1 mAb 3G4 light chain anti-human CD16", under the number CNCM 1-5458, or the E. coli cells which have been deposited at the CNCM (Collection Nationale de Cultures de Microorganismes) of Institut Pasteur on Nov. 25, 2019 under the name "pUC gamma1 variant N297A mAb 3G4 heavy chain anti-human CD16", under the number CNCM 1-5460.

Transformation can be performed by any known method for introducing polynucleotides into a cell host. Such methods are well known of the man skilled in the art and include dextran-mediated transformation, calcium phosphate precipitation, polybrene-mediated transfection, protoplast fusion, electroporation, encapsulation of the polynucleotide into liposomes, biolistic injection and direct microinjection of DNA into nuclei.

Mammalian cells are commonly used for the expression of a recombinant therapeutic immunoglobulins, especially for the expression of whole recombinant antibodies. For example, mammalian cells such as HEK293 or CHO cells, in conjunction with a vector containing the major intermediate early gene promoter element from human cytomegalovirus, are an effective system for expressing the IgG antibody of the invention.

It is preferred to choose a host cell which modulates the expression of the inserted sequences, or modifies and processes the gene product in the specific fashion desired. Such modifications (e.g., glycosylation) and processing of protein products may be important for the function of the protein. Appropriate cell lines or host systems are preferably chosen to ensure the correct modification and processing of the expressed antibody of interest. Hence, eukaryotic host cells which possess the cellular machinery for proper processing of the primary transcript, glycosylation of the gene product may be used. Such mammalian host cells include, but are not limited to, CHO, COS, HEK293, NS/0, BHK, Y2/0, 3T3 or myeloma cells (all these cell lines are available from public depositeries such as the Collection Nationale des Cultures de Microorganismes, Paris, France, or the American Type Culture Collection, Manassas, VA, U.S.A.).

For long-term, high-yield production of recombinant proteins, stable expression is preferred. In one embodiment of the invention, cell lines which stably express the antibody may be engineered. Rather than using expression vectors which contain viral origins of replication, host cells are transformed with DNA under the control of the appropriate expression regulatory elements, including promoters, enhancers, transcription terminators, polyadenylation sites, and other appropriate sequences known to the person skilled in art, and a selectable marker. Following the introduction of the foreign DNA, engineered cells may be allowed to grow for one to two days in an enriched media, and then are moved to a selective media. The selectable marker on the recombinant plasmid confers resistance to the selection and allows cells to stably integrate the plasmid into a chromosome and be expanded into a cell line. Other methods for constructing stable cell lines are known in the art. In particular, methods for site-specific integration have been developed. According to these methods, the transformed DNA under the control of the appropriate expression regulatory elements, including promoters, enhancers, transcription terminators, polyadenylation sites, and other appropriate sequences is integrated in the host cell genome at a specific target site which has previously been cleaved (U.S. Pat. Nos. 5,792,632; 5,830,729; 6,238,924; WO 2009/054985; WO 03/025183; WO 2004/067753).

A number of selection systems may be used according to the invention, including but not limited to the Herpes simplex virus thymidine kinase, hypoxanthine-guanine phosphoribosyltransferase, glutamate synthase selection in the presence of methionine sulfoximine and adenine phosphoribosyltransferase genes in tk, hgprt or aprt cells, respectively. Also, antimetabolite resistance can be used as the basis of selection for the following genes: dhfr, which confers resistance to methotrexate; gpt, which confers resistance to mycophenolic acid; neo, which confers resistance to the aminoglycoside, G-418; and hygro, which confers resistance to hygromycin. Methods known in the art of recombinant DNA technology may be routinely applied to select the desired recombinant clone, and such methods are described, for example, in Ausubel et al., eds., Current Protocols in Molecular Biology, John Wiley & Sons (1993). The expression levels of an antibody can be increased by vector amplification. When a marker in the vector system expressing an antibody is amplifiable, an increase in the level of inhibitor present in the culture will increase the number of copies of the marker gene. Since the amplified region is associated with the gene encoding the IgG antibody of the invention, production of said antibody will also increase. Alternative methods of expressing the gene of the invention exist and are known to the person of skills in the art. For example, a modified zinc finger protein can be engineered that is capable of binding the expression regulatory elements upstream of the gene of the invention; expression of the said engineered zinc finger protein (ZFN) in the host cell of the invention leads to increases in protein production. Moreover, ZFN can stimulate the integration of a DNA into a predetermined genomic location, resulting in high-efficiency site-specific gene addition.

The antibody of the invention may be prepared by growing a culture of the transformed host cells under culture conditions necessary to express the desired antibody. The resulting expressed antibody may then be purified from the culture medium or cell extracts. Soluble forms of the antibody of the invention can be recovered from the culture supernatant. It may then be purified by any method known in the art for purification of an immunoglobulin molecule, for example, by chromatography (e.g., ion exchange, affinity, particularly by Protein A affinity for Fc, and so on), centrifugation, differential solubility or by any other standard technique for the purification of proteins. Suitable methods of purification will be apparent to a person of ordinary skills in the art.

Another aspect of the invention thus relates to a method for the production of an antibody according to the invention, or antigen-binding fragments thereof, characterized in that said method comprises the following steps:

a) growing a host cell of the invention in an appropriate culture medium and b) recovering said antibody.

Pharmaceutical Composition

In another aspect, the invention relates to a pharmaceutical composition comprising the antibody of the invention, or antigen-binding fragments thereof. Preferably, the pharmaceutical composition of the invention contains, in addition to the antibody of the invention, various diluents, fillers, salts, buffers, stabilizers, solubilizers, and other materials well known in the art.

As used herein, "pharmaceutically acceptable carrier" includes any and all solvents, buffers, salt solutions, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of media and agents for pharmaceutically active substances is well known in the art. A typical pharmaceutical composition for intravenous infusion could be made up to contain 250 ml of sterile Ringer's solution, and 100 mg of the combination. Actual methods for preparing parenterally administrable compounds will be known or apparent to those skilled in the art and are described in more detail in for example, Remington's Pharmaceutical Science, 17th ed., Mack Publishing Company, Easton, Pa. (1985), and the 18th and 19th editions thereof, which are incorporated herein by reference.

The anti-CD16 antibody in the composition preferably is formulated in an effective amount. An "effective amount" refers to an amount effective, at dosages and for periods of time necessary, to achieve the desired result, such as prevention or treatment of amyloid plaque formation. A "therapeutically effective amount" means an amount sufficient to influence the therapeutic course of a particular disease state. A therapeutically effective amount is also one in which any toxic or detrimental effects of the agent are outweighed by the therapeutically beneficial effects.

According to another aspect, the invention relates to the anti-CD16 antibody of the invention, or antigen-binding fragments thereof, as a medicament. Also, the invention also relates to the pharmaceutical composition of the invention as a medicament.

Treatment Methods

As mentioned above, the antibodies of the present invention bind specifically to CD16A and CD16B with a high affinity. In addition, they are capable of inhibiting CD16-mediated intracellular signal transduction in monocytes and macrophages. The antibodies of the invention are particularly useful for preventing or treating CD16-related disorders. As used herein, the term "CD16-related disorders" refers to conditions or diseases resulting from the undesired activation of the CD16 signaling pathway. In other words, the term "CD16-related disorders" refers to conditions or diseases wherein CD16 is engaged.

Such conditions include a number of diseases, such as auto-immune disease, inflammatory disease, infectious disease (including graft-versus-host disease), and allergy.

It is easy for the skilled person to identify if a disease "engages CD16" or not, for example by analysing the expression level of CD16 at the surface of monocytes by flow cytometry (Gillis C M et al, 2017) or by identifying an abnormal copy number increase and/or mutations in the gene encoding CD16 (Breunis W B et al, 2009).

As used herein, the terms "treat," treating," "treatment," and the like refer to reducing or ameliorating the symptoms of a disorder (e.g., a CD16-related disorder) and/or symptoms associated therewith. It will be appreciated that, although not precluded, treating a disorder or condition does not require that the disorder, condition or symptoms associated therewith be completely eliminated.

As used herein "treating" a disease in a subject or "treating" a subject having a disease refers to subjecting the subject to a pharmaceutical treatment, e.g., the administration of a drug, such that the extent of the disease is decreased or prevented. For example, treating results in the reduction of at least one sign or symptom of the disease or condition. Treatment includes (but is not limited to) administration of a composition, such as a pharmaceutical composition, and may be performed either prophylactically, or subsequent to the initiation of a pathologic event. Treatment can require administration of an agent and/or treatment more than once.

A "subject" which may be subjected to said treatment described herein may be any of mammalian animals including human, dog, cat, cattle, goat, pig, swine, sheep and monkey. A human subject can be known as a patient. In one embodiment, "subject" or "patient" refers to a mammal affected by a disorder characterized by inappropriate activation of the CD16 signaling pathway, e.g. through hyperactivation or deregulation. A "control subject" refers to a mammal wherein the CD16 signaling pathway is correctly activated and regulated.

In one embodiment, the binding protein is administered to a subject with an autoimmune disease (i.e., a disease characterized by the production of autoantibodies). It is believed that pathogenic IgG antibodies observed in autoimmune diseases are either the pathogenic triggers for these diseases or contribute to disease progression and mediate disease through the inappropriate activation of cellular Fc receptors. Aggregated autoantibodies and/or autoantibodies complexed with self-antigens (immune complexes) bind to activating FcRs, thereby triggering the pathogenic sequelae of numerous autoimmune diseases (which occur in part because of immunologically mediated inflammation against self-tissues). Without intending to be bound by a particular mechanism of action, the CD16 antibodies described herein will interfere with and reduce the interaction of the autoimmune antibodies and FcγRIII receptors.

In these treatment methods, the antibodies of the invention are preferably divalent antibodies or divalent antigen-binding fragments thereof so as to efficiently block the CD16A and B receptors.

Examples of autoimmune diseases that can be treated include, without limitation, idiopathic thrombocytopenic purpura (ITP), rheumatoid arthritis (RA), autoimmune hemolytic anemia (AIHA), multiple sclerosis (MS), psoriasis, psoriatic arthritis, Reiter's syndrome, type 1 or immune mediated diabetes mellitus, inflammatory-bowel disease (IBD), chronic obstructive pulmonary disease (COPD) and pulmonary fibrosis.

Other examples of diseases or conditions that can be treated according to the invention also include any diseases susceptible to treatment with intravenous immunoglobulin (IVIG) therapy (e.g., allergic asthma). Thus, the treatment of autoimmune diseases heretofore treated by IVIG therapy (in one embodiment, a condition other than ITP) is contemplated. While detailed understanding of the mechanism of action of IVIG has not been established, it is proposed that modulating the activity of cellular FcγRs plays a role in its in vivo efficacy. The protective activity of IVIG may rely on the small percentage of dimeric or polymeric IgG present in the preparation. The specificity of the FcγRIII pathway in coupling cytotoxic and immune complex antibodies to effector responses and the ability to directly block this pathway with a mAb strongly suggests that an anti-FcγRIII antibody will have enhanced activity relative to IVIG.

Other examples of autoimmune disorders that may be treated by administering the antibodies of the present invention include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Bechet's disease, bullous pemphigoid, cardiomyopathy, celiac disease, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erythematosus, Meniere's disease, mixed connective tissue disease, multiple sclerosis, type 1 or immune mediated diabetes mellitus, myasthenia gravis, pemphigus vulgaris, pernicious anemia, polyarteritis nodosa, polychrondritis, polyglandular syndromes, polymyalgia rheumatics, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, takayasu arteritis, temporal arteritis giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephalitis, inflammatory-bowel disease (IBD), chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections.

Some autoimmune disorders are associated with an inflammatory condition. Thus, there is overlap between what is considered an autoimmune disorder and an inflammatory disorder. Therefore, some autoimmune disorders may also be characterized as inflammatory disorders. Examples of inflammatory disorders which can be prevented, treated or managed in accordance with the methods of the invention include, but are not limited to, asthma, encephalitis, inflammatory bowel disease (IBD), chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections.

In another embodiment, the present invention also relates to the use of an antibody or fragment or of a pharmaceutical composition according to the invention for the preparation of a drug and/or a medicament for the prevention or the treatment of any of the above-mentioned diseases engaging CD16A and/or CD16B.

According to a particular aspect, the antibody, or antigen-binding fragment thereof, or the pharmaceutical composition of the invention are for use in the prevention and/or in the treatment of diseases selected from the list consisting of: auto-immune disease, inflammatory disease, infectious disease, and allergy.

According to a particular embodiment, the antibody, or antigen-binding fragment thereof, or the pharmaceutical composition of the invention are for use in the prevention and/or in the treatment of an autoimmune disorder selected in the group consisting of: idiopathic thrombocytopenic purpura (ITP), rheumatoid arthritis (RA), autoimmune hemolytic anemia (AIHA), multiple sclerosis (MS), psoriasis, psoriatic arthritis, Reiter's syndrome, type 1 or immune mediated diabetes mellitus, inflammatory-bowel disease (IBD), chronic obstructive pulmonary disease (COPD) and pulmonary fibrosis.

In a particularly preferred embodiment, the antibody, or antigen-binding fragment thereof, or the pharmaceutical composition of the invention are for use in the prevention and/or in the treatment of idiopathic thrombocytopenic purpura (ITP), rheumatoid arthritis (RA) or autoimmune hemolytic anemia (AIHA). In an even more particular embodiment, the antibody, or antigen-binding fragment thereof, or the pharmaceutical composition of the invention are for use in the prevention and/or in the treatment of idiopathic thrombocytopenic purpura (ITP).

A reduction in a deleterious immune response can be detected as a reduction in inflammation. In a specific embodiment, an antibody reduces the inflammation in an animal by at least 99%, at least 95%, at least 90%, at least 85%, at least 80%, at least 75%, at least 70%, at 5 least 60%, at least 50%, at least 45%, at least 40%, at least 45%, at least 35%, at least 30%, at least 25%, at least 20%, or at least 10% relative to the inflammation in an animal in which said antibody has not been administered. Alternatively, a reduction in a deleterious immune response can be detected as a reduction in symptoms characteristic of the condition being treated (e.g., a reduction in symptoms exhibited by a subject suffering from an autoimmune condition), or by other criteria that will be easily recognized by physicians and experimentalists in the field of autoimmunity. It will be apparent that, in many cases, specific indicia of reduction will depend on the specific condition being treated. For example, for illustration and not limitation, a reduction in a deleterious immune response in a subject with ITP can be detected as a rise in platelet levels in the subject. Similarly, a reduction in a deleterious immune response in a subject with anemia can be detected as a rise in RBC levels in the subject. A clinician will recognize significant changes in platelet or RBC levels, or other responses following treatment.

In one aspect, the invention provides a method for treating an autoimmune disease, such as ITP, by administering an antibody or fragment that is largely devoid of effector function, as explained above.

In a related aspect, the invention provides methods of reducing a deleterious immune response in a mammal without significantly reducing neutrophil levels or inducing neutropenia (e.g., severe neutropenia or moderate neutropenia) by administering to the mammal a therapeutically effective amount of a pharmaceutical composition comprising the antibody or fragment described herein. In an embodiment, the mammal is human. In another embodiment, the mammal is a non-human mammal (e.g., mouse) comprising one or more human transgenes.

As used herein, "neutropenia" has its ordinary meaning, and refers to a state in which the number of neutrophils circulating in the blood is abnormally low. The normal level of neutrophils in human blood varies slightly by age and race. The average adult level is about 1500 cells/mm$^3$ of blood. Neutrophil counts less than 500 cells/mm$^3$ result in great risk of severe infection. Generally, in humans, severe neutropenia is defined by a blood neutrophil count less than about 500 cells/mm$^3$, and moderate neutropenia is characterized by a blood neutrophil count from about 500-1000 cells/mm$^3$.

The antibodies and fragments of the invention can be administered in combination with other treatments directed to alleviation of the deleterious immune response or its symptoms or sequelae. For example, they can be administered as part of a therapeutic regimen that includes co-administration of another agent or agents, e.g., a chemotherapeutic agent such as a non-steroidal anti-inflammatory drug (e.g., aspirin, ibuprofen), steroids (e.g., a corticosteroid, prednisone), immunosuppressants (e.g., cyclosporin A, methotrexate Cytoxan), and antibodies (e.g., in conjunction with IVIG).

The dosage of the compositions of the invention administered to a patient is typically about 0.1 mg/kg to about 10 mg/kg of the patient's body weight, e.g., about 0.1, about 0.2, about 0.3, about 0.4, about 0.5, about 0.6, about 0.7, about 0.8, about 0.9, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, and about 10 mg/kg of the patient's body weight. Preferably, the dosage administered to a patient is between about 1 mg/kg and about 9 mg/kg of the patient's body weight. In other embodiments the dosage of the compositions of the invention is about 0.1, about 0.3, about 1.0 or about 3.0 mg/kg of the patient's body weight.

The antibodies of the invention can be administered according to the judgment of the treating physician, e.g., daily, weekly, biweekly or at any other suitable interval, depending upon such factors, for example, as the nature of the ailment, the condition of the patient and half-life of the antibody. In a preferred example, a subject is treated with the antibody or fragment of the invention in the range of between about 0.1 to about 10 mg/kg body weight, one time per week for between about 1 to about 10 weeks, preferably between about 2 to about 8 weeks, more preferably between about 3 to about 7 weeks, and even more preferably for about 4, about 5, or about 6 weeks. In other embodiments, the pharmaceutical compositions of the invention are administered once a day, twice a day, or three times a day. In other embodiments, the pharmaceutical compositions are administered once a week, twice a week, once every two weeks, once a month, once every six weeks, once every two months, twice a year or once per year. It will also be appreciated that the effective dosage of the antibodies used for treatment may increase or decrease over the course of a particular treatment.

In a most preferred embodiment, the composition of the invention is administered intravenously over about 30 minutes. In other embodiments, the composition of the invention is administered intravenously over at least about 1 hour, at least about 30 minutes, or at least about 15 minutes.

More generally, for therapeutic applications, the anti-CD16 antibody of the invention can be administered to the subject as a bolus or by continuous infusion over a period of time, by intramuscular, intraperitoneal, intracerebrospinal, subcutaneous, intraarticular, intrasynovial, intrathecal, oral, topical, or inhalation routes.

The examples that follow are merely exemplary of the scope of this invention and content of this disclosure. One skilled in the art can devise and construct numerous modifications to the examples listed below without departing from the scope of this invention.

FIGURE LEGENDS

FIG. 1 shows the binding of the antibodies of the invention (the chimeric modified 3G4NA) on members of the hFcγR family, assessed by FACS. The member of the hFcγR family is indicated on top of the panels, as well as their potential polymorphism found in the human population. Grey histogram represents secondary antibody alone (background), whereas the black line represents primary and secondary antibody (binding of the antibody).

FIG. 2 shows the blocking activity of the antibodies of the invention (the chimeric modified 3G4NA) towards IgG (the ligand) on members of the hFcγR family, assessed by FACS. The member of the hFcγR family is indicated on top of the panels, as well as their potential polymorphism found in the human population. Grey histogram represents no staining (background), dotted line represents the binding of fluorescently-labelled human IgG-immune complexes and black line represents the binding of fluorescently-labelled human IgG-immune complexes in the presence of the chimeric mAb 3G4 N297A.

FIG. 3 discloses the variation of body central temperature observed after the injection of the antibodies of the invention (the chimeric modified 3G4NA-A), or after the injection of the antibodies of the prior art (chimeric 3G8-B or chimeric 3G8N297A-C) or controls (hIgG1 Herceptin) in hFcγR$^{KI}$ or mFcγR$^{null}$ mice. Statistical test: Two Way ANOVA (n=4 mice per group)

FIG. 4 discloses the variation of platelet numbers observed after the injection of the antibodies of the invention (the chimeric modified 3G4NA-A), or after the injection of the antibodies of the prior art (chimeric 3G8-B or chimeric 3G8N297A-C) or controls (hIgG1 Herceptin) in hFcγR$^{KI}$ or mFcγR$^{null}$ mice. Statistical test: t test with Mann-Whitney post-test (n=4 mice)

FIG. 5 discloses the variation of neutrophil numbers (CD11b+Ly6G+ cells) observed after the injection of the antibodies of the invention (the chimeric modified 3G4NA-A), or after the injection of the antibodies of the prior art (chimeric 3G8-B or chimeric 3G8N297A-C) or controls (hIgG1 Herceptin) in hFcγR$^{KI}$ or mFcγR$^{null}$ mice.

FIG. 6 discloses the variation of monocyte numbers (CD115+Ly6C+ cells) observed after the injection of the antibodies of the invention (the chimeric modified 3G4NA-A), or after the injection of the antibodies of the prior art (chimeric 3G8-B or chimeric 3G8N297A-C) or controls (hIgG1 Herceptin) in hFcγR$^{KI}$ or mFcγR$^{null}$ mice.

FIG. 7 shows the effect of the injection of the antibodies of the invention (the chimeric modified 3G4NA (9 mg/kg) on the platelet numbers in hFcγR$^{KI}$ mice when acute thrombocytopenia is induced subsequently (prophylactic treatment). Statistical test: t test with Mann-Whitney post-test.

FIG. 8 shows the effect of the injection of the antibodies of the invention (the chimeric modified 3G4NA, (9 mg/kg) on the platelet numbers in hFcγR$^{KI}$ mice A) when chronic thrombocytopenia has been induced previously (therapeutic treatment) with either an antibody that engages FcγR but not C1q (antibody 6A6KA), or B) with an antibody that engages both FcγR and C1q (antibody 6A6WT). Statistical test: Two Way ANOVA (n=4 mice per group).

EXAMPLES

1. Material and Methods

Antibodies and reagents. Recombinant hFcγRIIIA/CD16a variant V158 was purchased from R&D Systems, anti-mouse IgG Fc fragment HRP conjugated from Bethyl, anti-FLAG mAb, anti-human CD64 (clone 10.1), anti-human CD32B (clone AT10), anti-human CD16 (clone MEM-154), anti-mouse CD11b from BD Pharmingen, anti-human CD32A (clone IV.3) from StemCell Technologies, anti-mouse CD115 from Biolegend, anti-mouse Ly6G, anti-mouse Ly6C and anti-mouse CD45 from Miltenyi Biotec, PE-labelled F(ab')$_2$ Fragment Donkey Anti-Human IgG from Jackson Immuno Research.

Mice. BiozzyABH mice were purchased from Harlan laboratories. hFcγR$^{KI}$ (expressing hFcγRI, hFcγRIIA$_{H131}$, hFcγRIIB$_{I232}$, hFcγRIIC$_{stop13}$, hFcγRIIIA$_{V158}$ and hFcγRIIIB$_{NA2}$ polymorphic variants) and FcγR$^{null}$ mice (expressing no endogenous FcγR) were generated by Regeneron Pharmaceuticals Inc. as described previously (Beutier H. et al, 2018). All mice were bred at Institut Pasteur and used for experiments at 9-13 weeks of age, and starting 10-15 weeks for immunizations. All mice demonstrated normal development and breeding patterns. All animal care and experimentation were conducted in compliance with the guidelines and specific approval of the Animal Ethics committee CETEA (Institut Pasteur, Paris, France) registered under #2013-0103, and by the French Ministry of Research under agreement #00513.02.

Immunization of mice. BiozzyABH mice were injected intraperitoneally with 10 µg of recombinant hFcγRIIIA/CD16A variant V158 first in complete Freund adjuvant (CFA; Sigma Aldrich), then three times in incomplete Freund adjuvant (IFA) at 3-week intervals. Three weeks after the last immunization, a boost was performed by a intraperitoneal injection of 10 ug recombinant hFcγRIIIA/CD16A without adjuvant. Three days later the spleen was removed and splenocytes used for fusion and hybridoma generation using the ClonaCell™-HY Hybridoma kit (StemCell Technologies).

Screening of hybridomas. Specificity against hFcγRIIIA was tested for hybridomas by ELISA. 96-well plates (Costar) were coated with recombinant hFcγRIIIA/CD16A variant V158 at 1 µg/well in coupling buffer (50 nM carbonate-bicarbonate buffer at pH 9.6) at 4° C. for 16 h. Plates were washed 3 times with PBS Tween 0.01% (PBST), and blocked for 2 h at room temperature in PBST containing 3% BSA. Plates were washed 3 times before addition of 100 μl of supernatant from each hybridoma. After 2 hours, plates were washed with PBST and incubated with 1:4,000 of HRP-conjugated anti-mouse IgG Fc fragment for 1 h. Plates were washed 3 times with PBST before addition of 100 μL/well OPD peroxidase (Sigma). Reaction was stopped by addition of 100 μL 2M $H_2SO_4$ and absorbance was recorded at 492 nm and corrected at 620 nm.

Cloning. Sequencing of $V_H$ and $V_L$ DNA fragments, codon optimization for expression in human cells and synthesize were done by Eurofins. $V_H$ sequences were cloned into a human pUC19-Igγ1-expressing vector using SalI and AgeI restriction sites, and $V_L$ sequences were cloned into a human Igκ-expressing vector using AgeI and BsiWI restriction sites (a kind gift of Hugo Mouquet, Institut Pasteur, Paris). For the generation of an Fc-engineered mAb, a point mutation in the Igγ1-expressing vector was introduced at position 297 (N297A) to exchange an asparagine for an alanine using the QuickChange Site-Directed Mutagenesis Kit (Agilent Technologies). All vectors were sequenced before being used for antibody production.

Production of mAbs. The cDNA encoding the heavy chain (variable region; VH) of mAb 3G4 anti-human CD16 (human FcgammaRIII) fused to the cDNA encoding the heavy chain (constant regions; CH1-CH2-CH3) of human IgG1 harboring or not the N297A mutation leading to aglycosylation was inserted into a pUC expression vector (plasmid). These plasmids can be obtained by standard alkaline lysis followed by plasmid DNA precipitation and solubilization from the *E. coli* bacteria deposited on Nov. 25, 2019 at the Collection Nationale de Cultures de Microorganismes from Institut Pasteur under the numbers CNCM I-5459 (wild-type N297) or CNCM I-5460 (mutated N297A).

Similarly, the cDNA encoding the light chain (variable region; VL) of mAb 3G4 anti-human CD16 (human FcgammaRIII) fused to the cDNA encoding the human kappa light chain (kappa constant regions) was inserted into a pUC expression vector (plasmid). This plasmid can be obtained by standard alkaline lysis followed by plasmid DNA precipitation and solubilization from the *E. coli* bacteria deposited on Nov. 25, 2019 at the Collection Nationale de Cultures de Microorganismes from Institut Pasteur under the numbers CNCM I-5458.

Antibodies were produced by transient co-transfection of WT or N297A Fc-engineered mAb 3G4 heavy chain and mAb 3G4 light chain expression plasmids into exponentially growing Freestyle™ HEK 293-F that were cultured in serum-free Freestyle™ 293 Expression Medium (Life Technologies) in suspension at 37° C. in a humidified 8% $CO_2$ incubator on a shaker platform rotating at 110 rpm. Twenty-four hours before transfection, cells were harvested by centrifugation at 300×g for 5 min, and resuspended in Freestyle™ 293 expression medium at a density of $1×10^6$ cells/ml, and cultured overnight in the same conditions as mentioned above. For the production of mAbs, 40 μg of each $V_H$ and $V_L$ expressing plasmids were diluted in 80 μl of FectoPRO reagent (Polyplus) at a final DNA concentration of 0.8 μg/ml, incubated for 10 minutes at RT before addition to the cells. Twenty-four hours post-transfection, cells were diluted 1:1 with Freestyle™ 293 expression medium. Cells were cultured for 6 days after transfection, supernatants were harvested, centrifuged at 1800×g for 40 min and filtered (0.2 μm). Antibodies were purified by affinity chromatography using an AKTA pure FPLC instrument (GE Healthcare) on a HiTrap Protein G Column (GE Healthcare) and desalted on a HiTrap Desalting Column (GE Healthcare).

Assessment of Binding Specificity and Antagonistic Properties of Anti-hFcγRs Antibodies.

Specificity. A collection of Chinese Hamster Ovarian (CHO) cells expressing FLAG tagged human FcγR (Bruhns P. et al, 2009) was used to analyze the specificity of the antibody against the hFcγR family. Cells were incubated on ice for 30 min with mAbs at 1 μg/ml, washed 3 time in PBS containing 0.5% BSA and 2 mM EDTA (MACS buffer) and then incubated on ice for 30 min with 5 μg/ml PE-labelled F(ab')₂ Donkey Anti-Human IgG (Jackson ImmunoResearch). Data acquisition was performed on a MACSQuant flow cytometer (Miltenyi Biotec), and data analyzed using the Flowjo Software (FlowJo).

Antagonistic properties. hFcγR ligands, i.e. human IgG-immune complexes, were formed by incubating hIgG1 anti-dinitrophenyl (DNP) with BSA coupled to Trinitrophenyl (TNP) and to VT680 (BSA-TNP-VT680) at a 5:3 ratio for 30 min at 3TC in borate buffer saline. hFcγR-expressing CHO cells were pre-incubated or not on ice for 10 min with 10 μg/ml anti-hFcγRIII mAbs, then diluted 1:2 with human IgG-immune complexes (final concentration of 5 μg/ml hIgG1 anti-DNT and 3 μg/ml BSA-TNP-VT680) and incubated 30 min on ice. After 3 washes in MACS buffer, Data acquisition was performed on a MACSQuant flow cytometer and data analyzed using the Flowjo Software.

Surface Plasmon Resonance analysis. His-tagged ectodomains of hFcγRIIIA variant V158 were covalently immobilized on a His-tag capture sensor chip for a ProteON instrument (BioRad). A range of dilutions of anti-hFcγRIII mAbs were injected onto the chip. Background binding was measured on an empty HTE sensor chip channel and subtracted from the binding values observed on coated channels. The resulting sensorgrams were fitted using a "1:1 binding with mass transfer" model, and association ($K_{on}$), dissociation ($K_{off}$) constants and $K_D$ were calculated as the $K_{on}/K_{off}$ ratio using BIAevaluation 4.1 software.

Experimental immune thrombocytopenia. Acute immune thrombocytopenia was induced by injecting $hFcγR^{KI}$ or $FcγR^{null}$ mice with the depleting anti-platelet mAb 6A6, in a human IgG1 format (termed herein 6A6WT; 10 μg/mouse) or in a human IgG1 format, containing a Lysine to Alanine mutation at position 322 of the heavy chain to prevent complement component C1q binding (termed herein 6A6KA; 20 μg/mouse). Injection of 200 μg of irrelevant human IgG1 was used as control. Blood was drawn in EDTA and platelets counts were acquired with an ABC Vet automatic blood analyzer (HoribaABX). Baseline platelet counts were performed 3-5 days before the experiment. For prophylaxis experiments, mice were pretreated by intravenous injection of 9 mg/kg of anti-hFcγRIII mAbs 30 min before injection of the depleting anti-platelet mAb.

For therapeutic experiments, severe chronic thrombocytopenia was induced by repeated, daily injections of depleting anti-platelet mAbs, followed by concomitant injections of depleting anti-platelet mAbs and 9 mg/kg of mouse of anti-hFcγRIII mAbs.

Assessment of central body temperature. $hFcγR^{KI}$ and $FcγR^{null}$ mice were injected intravenously with indicated quantities of mAbs in 100 μL saline, or saline only as a control. Body temperature measurements were performed using a digital thermometer (YSI) with a rectal probe, 30 min before and at indicated timepoints for up to 120 min.

Analysis of neutrophil and monocyte populations. Four hours after intravenous injection of mAbs, blood samples were drawn in heparin and lysed using Lysis buffer (BD Pharmingen). Leucocytes were stained on ice 30 min with the following panel: CD45, CD115, Ly6G, Ly6C, CD11b and propidium iodure solution to characterize neutrophil (CD45+ CD11 b+ Ly6G+) and monocyte (CD45+ CD115+ Ly6C+) populations. After 3 washes in MACS buffer, cells were analyzed on MACSQuant flow cytometer, and data were analyzed using the Flowjo Software.

Statistical analyses. Data are presented as mean±SD. Central body temperature experiments were analyzed with Two Way ANOVA-multiple comparisons with Sidak test. Platelets numbers (FIG. 4), and prophylactic immune thrombocytopenia experiments were analyzed with t test with Mann-Whitney post-test (FIG. 7). Therapeutic immune thrombocytopenia experiments were analyzed with two way ANOVA-multiple comparisons with Sidak test (FIGS. 8.*a* and 8.*b*) Statistical analyses were performed using the Prism Software (GraphPad Software). P values<0.05 were considered statistically significant.

2. Results

2.1. Generation of the Hybridoma

The spleens of three mice immunized with recombinant ectodomains of CD16A V158 variant were used to generate hybridomas using standard fusion protocols. Hybridoma supernatants (>600 hybridomas tested) containing potential anti-CD16A antibodies were screened using an anti-CD16A V158 variant ELISA, followed by a flow cytometry screen using a collection of transfectant cells (deposited at CNCM) expressing the entire family of hFcγRs.

2.2. Sequencing of the CDRs and Important Regions of the Antibodies of the Invention

2.2.1. Murine Antibody of the Invention (3G4)

The CDRs expressed in the murine antibody produced by the hybridoma 3G4 have been characterized.

They have the following peptide sequences:

For the light chain:

```
CDR1 VL: QDIIKN = SEQ ID NO: 1

CDR2 VL: YAT = SEQ ID NO: 2

CDR3 VL: LQFYEFPYT = SEQ ID NO: 3
```

For the heavy chain:

```
CDR1 VH: GYTFIRNW = SEQ ID NO: 4

CDR2 VH: IDPSDGES = SEQ ID NO: 5

CDR3 VH: TRSRYYGGDWDWYFDV = SEQ ID NO :6
```

The 3G4 light chain variable domain amino acid sequence is depicted in SEQ ID NO:7 (CDRs underlined+Framework sequences):

```
DIVLTQSPSSISASLGDRITITCQATQDIIKNLNWYQQKPGKPPSFLI

YYATEVAEGVPSRFSGSGSGSDYSLTISNLESEDFADYYCLQFYEFPY

TFGGGTKLEIK
```

The 3G4 heavy chain variable domain amino acid sequence is depicted in SEQ ID NO:8 (CDRs underlined+Framework sequences):

```
GVQLQESGAELVRPGSSVKLSCKPSGYTFIRNWIHWVKQRPIQGLEWIG

AIDPSDGESHYNHKFTDKATLTVDKSSSTGYMQLNSLTSEDSAVYYCTR

SRYYGGDWDWYFDVWGTGTTVTVSS
```

Nucleotide sequences encoding variable domains of the light chain and the heavy chain of said murine antibody are respectively SEQ ID NO:9 (3G4 Light chain DNA sequence, CDRs+Framework sequences) and SEQ ID NO: 10 (3G4 Heavy chain DNA sequence, CDRs+Framework sequences).

2.2.2. Chimeric Mouse-Human Antibody of the Invention (Mouse-Human 3G4)

The $V_H$ mouse sequence of SEQ ID NO:10 of the anti-hFcγRIII monoclonal antibody has been inserted into a human IgG1 framework and the mouse $V_L$ sequence of SEQ ID NO:9 has been inserted into the human kappa light chain sequence.

The chimeric 3G4 of the invention is therefore a chimeric mouse-human IgG1 kappa antibody containing the mouse $V_H$ and mouse $V_L$ sequences of the anti-hFcγRIII mAb mouse clone 3G4.

The light chain of said chimeric antibody is of SEQ ID NO:11:

```
MGWSCIILFLVATATGVHSDIVLTQSPSSISASLGDRITITCQATQDII

KNLNWYQQKPGKPPSFLIYYATEVAEGVPSRFSGSGSGSDYSLTISNLE

SEDFADYYCLQFYEFPYTFGGGTKLEIKRTVAAPSVFIFPPSDEQLKSG

TASVVCLLNNFYPREAKVQWKVDNALQSGNSQESVTEQDSKDSTYSLSS

TLTLSKADYEKHKVYACEVTHQGLSSPVTKSFNRGEC*
```

The heavy chain of said chimeric antibody is of SEQ ID NO:12 (the N297 position is underlined):

```
MGWSCIILFLVATATGVHSEVQLQESGAELVRPGSSVKLSCKPSGYTFI

RNWIHWVKQRPIQGLEWIGAIDPSDGESHYNHKFTDKATLTVDKSSSTG

YMQLNSLTSEDSAVYYCTRSRYYGGDWDWYFDVWGTGTTVTVSSASTKG

PSVFPLAPSSKSTSGGTAALGCLVKDYFPEPVTVSWNSGALTSGVHTFP

AVLQSSGLYSLSSVVTVPSSSLGTQTYICNVNHKPSNTKVDKRVEPKSC

DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSR

WQQGNVFSCSVMHEALHNHYTQKSLSLSPGK*
```

Nucleotide sequences encoding the light chain and the heavy chain of said chimeric antibody are respectively SEQ ID NO:13 (chimeric 3G4 Light chain DNA sequence, CDRs+Framework sequences) and SEQ ID NO: 14 (chimeric 3G4 Heavy chain DNA sequence, CDRs+Framework sequences).

2.2.3. Chimeric Modified Mouse-Human Antibody of the Invention (Mouse-Human 3G4NA)

The chimeric anti-hFcγRIII mAb clone 3G4 has been generated as a modified format under the name "3G4NA" or "3G4N297A". 3G4NA is expressed as a chimeric mouse-human IgG1, kappa antibody mutated at position 297 of the heavy chain into an alanine (N297A mutation) and containing the mouse $V_H$ and mouse $V_L$ sequences of anti-hFcγRIII mAb mouse clone 3G4.

The light chain of said chimeric modified antibody 3G4NA is of SEQ ID NO:11:

MGWSCIILFLVATATGVHSDIVLTQSPSSISASLGDRITITCQATQDII

KNLNWYQQKPGKPPSFLIYYATEVAEGVPSRFSGSGSGSDYSLTISNLE

SEDFADYYCLQFYEFPYTFGGGTKLEIKRTVAAPSVFIFPPSDEQLKSG

TASVVCLLNNFYPREAKVQWKVDNALQSGNSQESVTEQDSKDSTYSLSS

TLTLSKADYEKHKVYACEVTHQGLSSPVTKSFNRGEC*

The heavy chain of said chimeric modified antibody 3G4NA is of SEQ ID NO:15: (the N297A mutation is underlined)

MGWSCIILFLVATATGVHSEVQLQESGAELVRPGSSVKLSCKPSGYTFI

RNWIHWVKQRPIQGLEWIGAIDPSDGESHYNHKFTDKATLTVDKSSSTG

YMQLNSLTSEDSAVYYCTRSRYYGGDWDWYFDVWGTGTTVTVSSASTKG

PSVFPLAPSSKSTSGGTAALGCLVKDYFPEPVTVSWNSGALTSGVHTFP

AVLQSSGLYSLSSVVTVPSSSLGTQTYICNVNHKPSNTKVDKRVEPKSC

DKTHTCPPCPAPELLGGPSVFLFPPKPKDTLMISRTPEVTCVVVDVSHE

DPEVKFNWYVDGVEVHNAKTKPREEQY<u>A</u>STYRVVSVLTVLHQDWLNGKE

YKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSR

WQQGNVFSCSVMHEALHNHYTQKSLSLSPGK*

Nucleotide sequences encoding the light chain and the heavy chain of said chimeric antibody are respectively SEQ ID NO:13 (chimeric 3G4NA Light chain DNA sequence, CDRs+Framework sequences) and SEQ ID NO: 16 (chimeric 3G4NA Heavy chain DNA sequence, CDRs+Framework sequences).

2.3. In Vitro Characterization of mAb 3G4 Using a Collection of CHO-K1 Transfectant Cells Expressing Each a Different Human FcγR

2.3.1. Specificity of the Chimeric Modified Antibody 3G4NA to its Targets

The specificity of the chimeric modified antibody 3G4NA towards the members of the hFcγR family has been assessed as exposed in the Material & Methods part, in CHO cells expressing FLAG tagged human FcγR. The cells were incubated with 3G4NA mAbs at 1 μg/ml, washed and then incubated on ice for 30 min with 5 μg/ml PE-labelled F(ab')$_2$ Donkey Anti-Human IgG. The FACS results are disclosed on FIG. 1.

It is important to note that the antibody is specific for his target, with only an expected unspecific binding of mAb 3G4 $N_{297}A$ to hFcγRI in the family, as observed with all human IgG1 antibodies in the $N_{297}A$ format. This binding is due to the affinity of hFcγRI for the Fc portion of mAb 3G4 $N_{297}A$. This binding to hFcγRI will however not induce any side effects in vivo, since human sera contain only 8-15 mg/mL of IgG (The 3G4NA antibody will compete with circulating human IgGs of the patient to bind hFcγRI but hFcγRI will be completely or totally occupied, saturated with endogenous IgGs. The 3G4 antibody of the invention can therefore not be "captured" by hFcγRI, which is much less expressed relative to hFcγRIII).

2.3.2. Blocking Ability of the Antibody to Prevent Binding of IgG (the Ligand) to FcγRIII (the Receptors)

The blocking properties of the chimeric modified antibody 3G4NA towards the members of the hFcγR family has also been assessed as detailed above. This time, the cells were incubated with 3G4NA mAbs at 10 μg/ml.

The FACS results are disclosed on FIG. 2.

It shows a very efficient blockade of human IgG immune complex binding to the hFcγRIII family in the presence of the chimeric mAb 3G4 $N_{297}A$. The blockade is less efficient on hFcγRIIIA V158, the polymorphic variant of hFcγRIIIA with higher affinity binding to human IgG1.

2.3.3. Affinities of the Antibody Formats for their Respective Targets by Surface Plasmon Resonance Analysis.

The affinity of the antibodies of the invention for the hFcγRIIIA (V158 variant) has been assessed by SPR as detailed above. The results are provided in Table 3:

TABLE 3

| affinity of the antibodies of the invention towards hFcγRIIIA | | | |
|---|---|---|---|
| Chimeric 3G4 hIgG1 | Chimeric 3G4 hIgG1 $N_{297}A$ format | Chimeric 3G8 hIgG1 | Chimeric 3G8 hIgG1 $N_{297}A$ format |
| $K_D$ (nM) $7.9 \pm 1.2$ | $16.0 \pm 0.9$ | $2.1 \pm 1.6$ | $2.88 \pm 1.2$ |
| $K_{on}$ (1/Ms) $1.3 \times 10^5$ | $1.9 \times 10^4$ | $3.0 \times 10^5$ | $1.1 \times 10^5$ |
| $K_{off}$ (1/s) $1.0 \times 10^{-3}$ | $3.4 \times 10^{-4}$ | $2.1 \times 10^{-4}$ | $3.0 \times 10^{-4}$ |

This Table shows that both mAb 3G4 expressed as a human IgG1 format (chimeric antibody) or as a human IgG1 format bearing a $N_{297}A$ mutation (chimeric and modified antibody) bind hFcγRIIIA (V158 variant) with an affinity close to 10 nM. These high affinities are compatible with a therapeutic use of these antibodies in vivo in humans or animals.

2.4. In Vivo Evaluation of the Antibodies of the Invention

2.4.1. Assessment of the Body Temperature

Mice expressing human IgG receptors (hFcγRI, hFcγRIIA (H131), hFcγRIIB, hFcγRIIIA(V158), hFcγRIIIB(NA2)) in place of their endogenous IgG receptors (hFcγR$^{KI}$ mice) (Beutier H, et al. Science Immunol. 2018) were treated by injection of 9 mg/kg of one of the antibodies listed below. As a negative control, mice expressing no endogenous FcγRs (FcγR$^{null}$) were also injected:

Chimeric and modified 3G4 (hIgG1 $N_{297}A$ format)
Chimeric and modified 3G8 (hIgG1 $N_{297}A$ format)
Chimeric WT 3G8 hIgG1
hIgG1 Herceptin (negative control=irrelevant antibody)
Read out corresponding to potential adverse effects:
Body temperature: every 10 minutes after injection and up to 120 minutes
Platelets number: 4 h after injection
Blood neutrophil and monocyte numbers: 4 h after injection The results are disclosed on FIG. 3.

As shown on FIG. 3, no significant variation in central temperature observed after the chimeric modified mAb 3G4 hIgG1 $N_{297}A$ injection, whereas a significant drop occurred in central body temperature after mAb 3G8 hIgG1 or after mAb 3G8 hIgG1 $N_{297}A$ injection. This temperature drop is reminiscent of anaphylactic reactions or adverse drug reactions 2.4.2. Assessment of the Platelets Number Mice expressing human IgG receptors (hFcγRI, hFcγRIIA (H131), hFcγRIIB, hFcγRIIIA(V158), hFcγRIIIB(NA2)) in place of their endogenous IgG receptors (hFcγR$^{KI}$ mice) (Beutier H, et al. Science Immunol. 2018) were treated by injection of 9 mg/kg of one of the antibodies listed below. As a negative control, mice expressing no endogenous FcγRs (FcγR$^{null}$) were also injected:

Chimeric and modified 3G4 (hIgG1 $N_{297}A$ format)
Chimeric and modified 3G8 (hIgG1 $N_{297}A$ format)
Chimeric WT 3G8 hIgG1
hIgG1 Herceptin (negative control=irrelevant antibody)
The results are disclosed on FIG. 4.

As disclosed on FIG. 4, no significant variation in platelet numbers observed after the chimeric and modified mAb 3G4 hIgG1 $N_{297}A$ injection, but significant thrombocytopenia was observed after administration of mAb 3G8 hIgG1 both in hFcγR$^{KI}$ mice or in FcγR$^{null}$ mice. These adverse effects are prevented by using the mAb 3G8 hIgG1 $N_{297}A$ mutant, suggestive that FcγR and complement may be responsible for platelet removal/destruction.

2.4.3. Neutrophil and Monocyte Populations

Four hours after intravenous injection of the mAbs of the invention and control antibodies, blood samples were collected. Leucocytes were stained to characterize neutrophil (CD45+CD11b+Ly6G+—FIG. 5) and monocyte (CD45+ CD115+Ly6C+—FIG. 6) populations. After 3 washes, the cells were analyzed by FACS.

As disclosed on FIGS. 5 and 6, no significant variation in neutrophil or monocyte numbers was observed after injection of the chimeric and modified mAb 3G4 hIgG1 $N_{297}A$ of the invention, of the mAb 3G8 hIgG1 or of the mAb 3G8 hIgG1 $N_{297}A$.

2.5. In Vivo Characterization of mAb 3G4 Blocking Antibody on IgG-Dependent Preclinical Disease Models 2.5.1. Injection of the Blocking Chimeric Modified mAb 3G4 (hIgG1 $N_{297}A$ Format) can Prevent the Induction of Thrombocytopenia.

Immune thrombocytopenia was induced by injecting hFcγR$^{KI}$ or FcγR$^{null}$ mice with the depleting anti-platelet mAb 6A6, in a human IgG1 format (termed herein 6A6WT; 10 μg/mouse) or in a human IgG1 format, containing a Lysine to Alanine mutation at position 322 of the heavy chain to prevent complement component C1q binding (termed herein 6A6KA; 20 μg/mouse). Injection of 200 μg of irrelevant human IgG1 was used as control.

For prophylaxis experiments, mice were pretreated by intravenous injection of 9 mg/kg of mouse of anti-hFcγRIII mAbs 30 min before the injection of the depleting anti-platelet mAb.

The FIG. 7 shows the results obtained on eight hFcγR$^{KI}$ mice (n=4 per group).

A significant protection from IgG-induced thrombocytopenia was observed when using the chimeric modified mAb 3G4 of the invention (IgG1 $N_{297}A$ format).

2.5.2. Injection of the Blocking Chimeric Modified mAb 3G4 (IgG1 $N_{297}A$ Format) can Treat Thrombocytopenia.

For therapeutic experiments, severe chronic thrombocytopenia was induced in the above-mentioned mice by repeated daily injections of depleting anti-platelet mAbs followed by concomitant injections of depleting anti-platelet mAbs 6A6KA (20 μg/mouse) and 9 mg/kg of mouse of anti-hFcγRIII mAbs.

In a first experiment, the anti-platelet mAb used (6A6KA) engages FcγR but not C1q.

The FIG. 8A shows that, under these chronic thrombocytopenia conditions, injections of the chimeric modified 3G4 (hIgG1$N_{297}A$ format) allow the restauration of normal circulating platelet numbers, 48 h after the start of therapeutic treatment.

In a second experiment, the anti-platelet mAb 6A6WT engages both FcγR and C1q (chronic injections of 6A6WT (10 μg/mouse).

The FIG. 8B shows that, also under these chronic thrombocytopenia conditions, injections of the chimeric modified 3G4 (hIgG1 $N_{297}A$ format) allow restauration of normal circulating platelet numbers, 48 h after the start of therapeutic treatment.

BIBLIOGRAPHIC REFERENCES

Altschul et al., (1997) Nucleic Acids Res. 25:3389-3402

Beutier H, Hechler B, Godon O, et al. Platelets expressing IgG receptor FcgammaRIIA/CD32A determine the severity of experimental anaphylaxis. Sci Immunol. 2018; 3(22).

Breunis W B, van Mirre E, Geissler J, Laddach N, Wolbink G, van der Schoot E, de Haas M, de Boer M, Roos D, Kuijpers T W. Copy number variation at the FCGR locus includes FCGR3A, FCGR2C and FCGR3B but not FCGR2A and FCGR2B. Blood. 2008 Feb. 1; 111(3): 1029-38

Bruhns P, Iannascoli B, England P, et al. Specificity and affinity of human Fcγ receptors and their polymorphic variants for human IgG subclasses. Blood. 2009; 113: 3716-3725.

Bruhns P, Jonsson F. Mouse and human FcR effector functions. Immunol Rev. 2015; 268(1):25-51.

Bussel J B, Patel V, Dunbar C, et al. GMA161 Treatment of Refractory ITP: Efficacy of Fcγ-RIII Blockade. Blood. 2006; 108(11):1074-1074.

Chaturvedi S, Arnold D M, McCrae K R. Splenectomy for immune thrombocytopenia: down but not out. Blood. 2018; 131(11):1172-1182.

Chong B H. Primary immune thrombocytopenia: understanding pathogenesis is the key to better treatments. J Thromb Haemost. 2009; 7(2):319-321.

Clarkson S B, Bussel J B, Kimberly R P, Valinsky J E, Nachman R L, Unkeless J C. Treatment of refractory immune thrombocytopenic purpura with an anti-Fc gamma-receptor antibody. N Engl J Med. 1986; 314(19): 1236-1239.

Dall'Acqua W F, Woods R M, Ward E S, Palaszynski S R, Patel N K, Brewah Y A, Wu H, Kiener P A, Langermann S (2002) Increasing the affinity of a human IgG1 for the neonatal Fc receptor: biological consequences. J Immunol 169: 5171-80.

in Dayhoff et al. (1978), "A model of evolutionary change in proteins", "Atlas of Protein Sequence and Structure," Vol. 5, Suppl. 3 (ed. M. O. Dayhoff), pp. 345-352. Natl. Biomed. Res. Found., Washington, D.C.

Finkelman F D. Anaphylaxis: lessons from mouse models. J Allergy Clin Immunol. 2007; 120(3):506-515; quiz 516-507.

Flaherty M M, MacLachlan T K, Troutt M, et al. Nonclinical evaluation of GMA161—an antihuman CD16 (FcgammaRIII) monoclonal antibody for treatment of autoimmune disorders in CD16 transgenic mice. Toxicol Sci. 2012; 125(1):299-309.

Fleit H B, Wright S D, Unkeless J C. Human neutrophil Fc gamma receptor distribution and structure. Proc Natl Acad Sci USA. 1982; 79(10):3275-3279.

Foster C B, Zhu S, Erichsen H C, Lehrnbecher T, Hart E S, Choi E, Stein S, Smith M W, Steinberg S M, Imbach P, Kühne T, Chanock S J, for the Early Chronic ITPSG (2001) Polymorphisms in inflammatory cytokines and Fcγ receptors in childhood chronic immune thrombocytopenic purpura: a pilot study. British Journal of Haematology 113: 596-599

Fujimoto T-T, Inoue M, Shimomura T, Fujimura K (2001) Involvement of Fcγ receptor polymorphism in the therapeutic response of idiopathic thrombocytopenic purpura. British Journal of Haematology 115: 125-130

Gillis C, Gouel-Cheron A, Jonsson F, Bruhns P (2014) Contribution of Human FcgammaRs to Disease with Evidence from Human Polymorphisms and Transgenic Animal Studies. Front Immunol 5: 254

Gillis C M, Gouel-Chéron A, Bruhns P. Anaphylaxis (Immediate Hypersensitivity): From Old to New Mechanisms. Encyclopedia of Inflammatory Diseases. 2015.

Gillis C M, Jönsson F, Mancardi D A, Tu N, Beutier H, Van Rooijen N, Macdonald L E, Murphy A J, Bruhns P. Mechanisms of anaphylaxis in human low-affinity IgG receptor locus knock-in mice. J Allergy Clin Immunol. 2017 April; 139(4):1253-1265

Henikoff et al. (1992) Proc. Natl. Acad. Sci. USA 89:10915-10919

Kistangari G, McCrae K R. Immune thrombocytopenia. Hematol Oncol Clin North Am. 2013; 27(3):495-520.

Lee C H et al., An engineered human Fc domain that behaves like a pH-toggle switch for ultra-long circulation persistence. Nat Commun. 2019 Nov. 6; 10(1):5031.

Lefranc, M.-P., et al., IMGT unique numbering for MHC groove G-DOMAIN and MHC superfamily (MhcSF) G-LIKE-DOMAIN. Dev. Comp. Immunol., 27, 55-77 (2003)

Li J, van der Wal D E, Zhu G, et al. Desialylation is a mechanism of Fc-independent platelet clearance and a therapeutic target in immune thrombocytopenia. Nat Commun. 2015; 6:7737.

Najean Y, Rain J D, Billotey C. The site of destruction of autologous 111In-labelled platelets and the efficiency of splenectomy in children and adults with idiopathic thrombocytopenic purpura: a study of 578 patients with 268 splenectomies. Br J Haematol. 1997; 97(3):547-550.

Nakar C T, Bussel J B. 3G8 and GMA161, Anti FcγRIII Inhibitory Monoclonal Antibodies in the Treatment of Chronic Refractory ITP. (Summary of 2 Pilot Studies). Blood. 2009; 114:2404.

Portielje J E, Westendorp R G, Kluin-Nelemans H C, Brand A. Morbidity and mortality in adults with idiopathic thrombocytopenic purpura. Blood. 2001; 97(9):2549-2554.

Rodeghiero F, Stasi R, Gernsheimer T, et al. Standardization of terminology, definitions and outcome criteria in immune thrombocytopenic purpura of adults and children: report from an international working group. Blood. 2009; 113(11):2386-2393.

Shields R L, et al. High resolution mapping of the binding site on human IgG1 for Fc gamma RI, Fc gamma RII, Fc gamma RIII, and FcRn and design of IgG1 variants with improved binding to the Fc gamma R. J Biol Chem 2001; 276:6591-6604

Zalevsky J, Chamberlain A K, Horton H M, Karki S, Leung I W, Sproule T J, Lazar G A, Roopenian D C, Desjarlais J R. Enhanced antibody half-life improves in vivo activity. Nat Biotechnol. 2010 February; 28(2):157-9

The invention claimed is:

1. An antagonistic antibody against CD16 or an antigen-binding fragment thereof, said antibody comprising:
 a) a light chain comprising a CDR-L1, CDR-L2 and CDR-L3 having respectively the amino acid sequences SEQ ID NO: 1, 2 and 3; and
 b) a heavy chain comprising a CDR-H1, CDR-H2 and CDR-H3 having respectively the amino acid sequences SEQ ID NO: 4, 5 and 6.

2. An antagonistic antibody against CD16 or an antigen-binding fragment thereof, said antibody comprising:
 a) a light chain comprising a CDR-L1, CDR-L2 and CDR-L3 having respectively the amino acid sequences SEQ ID NO: 1, 2 and 3, with no more than a single amino acid change in only one of CDR-L1, CDR-L2, or CDR-L3; and
 b) a heavy chain comprising a CDR-H1, CDR-H2 and CDR-H3 having respectively the amino acid sequences SEQ ID NO: 4, 5 and 6.

3. The antagonistic antibody of claim 1, wherein said antibody binds specifically to the extracellular domain of CD16A and CD16B on monocytes, macrophages, NK cells and neutrophils, without inducing intracellular signal events in said cells.

4. The antibody or fragment of claim 1, wherein the dissociation constant (KD) of said antibody or fragment with CD16AV158 is comprised between 5 nM and 20 nM measured by Surface Plasmon Resonance.

5. The antibody or fragment of claim 1, wherein it is a chimeric or humanized antibody that has been recombinantly modified by introducing a N297A mutation in the human IgG1 heavy chain.

6. A pharmaceutical composition comprising the antibody or fragment according to claim 1, and a pharmaceutically-acceptable carrier.

7. A kit comprising the antibody or fragment according to claim 1 and means for detecting said antibody or fragment when bound to CD16A or CD16B.

8. The kit of claim 7, wherein said antibody or fragment is conjugated to a labelling molecule, and said means comprise film sensitive to the radio- or chemi-luminescent label, or wherein said antibody or fragment is conjugated to a labelling tag molecule such as histidine or c-myc tag, and said means comprise an antibody which recognizes said tag molecule.

9. The antibody or fragment according to claim 1, wherein it is conjugated to a toxin molecule such as a ribosyl transferase, serine protease, guanyl cyclase activator, calmodulin-dependent adenyl cyclase, ribonuclease, DNA alkylating agent or mitosis inhibitor.

10. The antibody or fragment of claim 2, wherein it is a chimeric or humanized antibody that has been recombinantly modified by introducing a N297A mutation in the human IgG1 heavy chain.

11. A kit comprising the antibody or fragment according to claim 2 and means for detecting said antibody or fragment when bound to CD16A or CD16B.

12. The kit of claim 11, wherein said antibody or fragment is conjugated to a labelling molecule, and said means comprise film sensitive to the radio- or chemi-luminescent label, or wherein said antibody or fragment is conjugated to a labelling tag molecule such as histidine or c-myc tag, and said means comprise an antibody which recognizes said tag molecule.

13. The antibody or fragment according to claim 2, wherein it is conjugated to a toxin molecule such as a ribosyl transferase, serine protease, guanyl cyclase activator, calmodulin-dependent adenyl cyclase, ribonuclease, DNA alkylating agent or mitosis inhibitor.

* * * * *

SEQUENCE LISTING

```
<160> NUMBER OF SEQ ID NOS: 21

<210> SEQ ID NO 1
<211> LENGTH: 6
<212> TYPE: PRT
<213> ORGANISM: mus musculus

<400> SEQUENCE: 1

Gln Asp Ile Ile Lys Asn
1               5

<210> SEQ ID NO 2
<211> LENGTH: 3
<212> TYPE: PRT
<213> ORGANISM: mus musculus

<400> SEQUENCE: 2

Tyr Ala Thr
1

<210> SEQ ID NO 3
<211> LENGTH: 9
<212> TYPE: PRT
<213> ORGANISM: mus musculus

<400> SEQUENCE: 3

Leu Gln Phe Tyr Glu Phe Pro Tyr Thr
1               5
```

-continued

```
<210> SEQ ID NO 4
<211> LENGTH: 8
<212> TYPE: PRT
<213> ORGANISM: mus musculus

<400> SEQUENCE: 4

Gly Tyr Thr Phe Ile Arg Asn Trp
1               5

<210> SEQ ID NO 5
<211> LENGTH: 8
<212> TYPE: PRT
<213> ORGANISM: mus musculus

<400> SEQUENCE: 5

Ile Asp Pro Ser Asp Gly Glu Ser
1               5

<210> SEQ ID NO 6
<211> LENGTH: 16
<212> TYPE: PRT
<213> ORGANISM: mus musculus

<400> SEQUENCE: 6

Thr Arg Ser Arg Tyr Tyr Gly Gly Asp Trp Asp Trp Tyr Phe Asp Val
1               5                   10                  15

<210> SEQ ID NO 7
<211> LENGTH: 107
<212> TYPE: PRT
<213> ORGANISM: mus musculus

<400> SEQUENCE: 7

Asp Ile Val Leu Thr Gln Ser Pro Ser Ser Ile Ser Ala Ser Leu Gly
1               5                   10                  15

Asp Arg Ile Thr Ile Thr Cys Gln Ala Thr Gln Asp Ile Ile Lys Asn
            20                  25                  30

Leu Asn Trp Tyr Gln Gln Lys Pro Gly Lys Pro Pro Ser Phe Leu Ile
        35                  40                  45

Tyr Tyr Ala Thr Glu Val Ala Glu Gly Val Pro Ser Arg Phe Ser Gly
    50                  55                  60

Ser Gly Ser Gly Ser Asp Tyr Ser Leu Thr Ile Ser Asn Leu Glu Ser
65                  70                  75                  80

Glu Asp Phe Ala Asp Tyr Tyr Cys Leu Gln Phe Tyr Glu Phe Pro Tyr
                85                  90                  95

Thr Phe Gly Gly Gly Thr Lys Leu Glu Ile Lys
            100                 105

<210> SEQ ID NO 8
<211> LENGTH: 123
<212> TYPE: PRT
<213> ORGANISM: mus musculus

<400> SEQUENCE: 8

Gly Val Gln Leu Gln Glu Ser Gly Ala Glu Leu Val Arg Pro Gly Ser
1               5                   10                  15

Ser Val Lys Leu Ser Cys Lys Pro Ser Gly Tyr Thr Phe Ile Arg Asn
            20                  25                  30

Trp Ile His Trp Val Lys Gln Arg Pro Ile Gln Gly Leu Glu Trp Ile
        35                  40                  45
```

-continued

```
Gly Ala Ile Asp Pro Ser Asp Gly Glu Ser His Tyr Asn His Lys Phe
    50              55                  60

Thr Asp Lys Ala Thr Leu Thr Val Asp Lys Ser Ser Ser Thr Gly Tyr
65              70                  75                  80

Met Gln Leu Asn Ser Leu Thr Ser Glu Asp Ser Ala Val Tyr Tyr Cys
                85                  90                  95

Thr Arg Ser Arg Tyr Tyr Gly Gly Asp Trp Asp Trp Tyr Phe Asp Val
            100                 105                 110

Trp Gly Thr Gly Thr Thr Val Thr Val Ser Ser
        115                 120
```

<210> SEQ ID NO 9
<211> LENGTH: 321
<212> TYPE: DNA
<213> ORGANISM: mus musculus

<400> SEQUENCE: 9

```
gacattgtgc tgacccagtc tccatcctct atatctgcat ctctgggaga cagaataacc    60
atcacttgcc aggcaactca agacattatt aagaatttga attggtatca gcagaaacca   120
gggaaacccc cttcattcct gatctattat gcaactgaag tggcagaagg ggtcccatca   180
aggttcagtg gcagtgggtc tgggtcagac tattctctga caatcagcaa cctggagtct   240
gaagattttg cagactatta ctgtctacag ttttatgagt ttccgtacac gttcggaggg   300
gggaccaagc tggaaataaa a                                              321
```

<210> SEQ ID NO 10
<211> LENGTH: 369
<212> TYPE: DNA
<213> ORGANISM: mus musculus

<400> SEQUENCE: 10

```
ggggtgcagc tgcaggagtc tggggctgaa ctggtgaggc ctgggtcttc agtgaaactg    60
tcctgcaagc cttctggcta caccttcatc agaaattgga tacattgggt gaagcagagg   120
cctatccaag gccttgaatg gattggtgcc attgaccctt ctgatggtga atctcactac   180
aatcacaaat tcacggacaa ggccacattg actgtagaca gtcctccag cacaggctac   240 atgcaactca acagcctgac atctgaggac tctgcggtct actactgtac aagatcgaga   300
tactacggtg tgactgggga ctggtacttc gatgtctggg gcacagggac cacggtcacc   360
gtctcctca                                                           369
```

<210> SEQ ID NO 11
<211> LENGTH: 233
<212> TYPE: PRT
<213> ORGANISM: artificial
<220> FEATURE:
<223> OTHER INFORMATION: aminoacid sequence of the light chain of
      chimeric antibody 3G4

<400> SEQUENCE: 11

```
Met Gly Trp Ser Cys Ile Ile Leu Phe Leu Val Ala Thr Ala Thr Gly
1               5                   10                  15

Val His Ser Asp Ile Val Leu Thr Gln Ser Pro Ser Ser Ile Ser Ala
                20                  25                  30

Ser Leu Gly Asp Arg Ile Thr Ile Thr Cys Gln Ala Thr Gln Asp Ile
        35                  40                  45

Ile Lys Asn Leu Asn Trp Tyr Gln Gln Lys Pro Gly Lys Pro Pro Ser
    50              55                  60
```

```
Phe Leu Ile Tyr Tyr Ala Thr Glu Val Ala Glu Gly Val Pro Ser Arg
65                  70                  75                  80

Phe Ser Gly Ser Gly Ser Gly Ser Asp Tyr Ser Leu Thr Ile Ser Asn
                85                  90                  95

Leu Glu Ser Glu Asp Phe Ala Asp Tyr Tyr Cys Leu Gln Phe Tyr Glu
            100                 105                 110

Phe Pro Tyr Thr Phe Gly Gly Gly Thr Lys Leu Glu Ile Lys Arg Thr
            115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 12
<211> LENGTH: 472
<212> TYPE: PRT
<213> ORGANISM: artificial
<220> FEATURE:
<223> OTHER INFORMATION: amino acid sequence of the heavy chain of
      chimeric 3G4

<400> SEQUENCE: 12

Met Gly Trp Ser Cys Ile Ile Leu Phe Leu Val Ala Thr Ala Thr Gly
1               5                   10                  15

Val His Ser Glu Val Gln Leu Gln Glu Ser Gly Ala Glu Leu Val Arg
            20                  25                  30

Pro Gly Ser Ser Val Lys Leu Ser Cys Lys Pro Ser Gly Tyr Thr Phe
            35                  40                  45

Ile Arg Asn Trp Ile His Trp Val Lys Gln Arg Pro Ile Gln Gly Leu
    50                  55                  60

Glu Trp Ile Gly Ala Ile Asp Pro Ser Asp Gly Glu Ser His Tyr Asn
65                  70                  75                  80

His Lys Phe Thr Asp Lys Ala Thr Leu Thr Val Asp Lys Ser Ser Ser
                85                  90                  95

Thr Gly Tyr Met Gln Leu Asn Ser Leu Thr Ser Glu Asp Ser Ala Val
            100                 105                 110

Tyr Tyr Cys Thr Arg Ser Arg Tyr Tyr Gly Gly Asp Trp Asp Trp Tyr
            115                 120                 125

Phe Asp Val Trp Gly Thr Gly Thr Thr Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
```

-continued

```
              180             185             190
His Thr Phe Pro Ala Val Leu Gln Ser Ser Gly Leu Tyr Ser Leu Ser
         195             200             205

Ser Val Val Thr Val Pro Ser Ser Ser Leu Gly Thr Gln Thr Tyr Ile
    210             215             220

Cys Asn Val Asn His Lys Pro Ser Asn Thr Lys Val Asp Lys Arg Val
225             230             235             240

Glu Pro Lys Ser Cys Asp Lys Thr His Thr Cys Pro Pro Cys Pro Ala
             245             250             255

Pro Glu Leu Leu Gly Gly Pro Ser Val Phe Leu Phe Pro Pro Lys Pro
         260             265             270

Lys Asp Thr Leu Met Ile Ser Arg Thr Pro Glu Val Thr Cys Val Val
         275             280             285

Val Asp Val Ser His Glu Asp Pro Glu Val Lys Phe Asn Trp Tyr Val
    290             295             300

Asp Gly Val Glu Val His Asn Ala Lys Thr Lys Pro Arg Glu Glu Gln
305             310             315             320

Tyr Asn Ser Thr Tyr Arg Val Val Ser Val Leu Thr Val Leu His Gln
             325             330             335

Asp Trp Leu Asn Gly Lys Glu Tyr Lys Cys Lys Val Ser Asn Lys Ala
         340             345             350

Leu Pro Ala Pro Ile Glu Lys Thr Ile Ser Lys Ala Lys Gly Gln Pro
         355             360             365

Arg Glu Pro Gln Val Tyr Thr Leu Pro Pro Ser Arg Glu Glu Met Thr
    370             375             380

Lys Asn Gln Val Ser Leu Thr Cys Leu Val Lys Gly Phe Tyr Pro Ser
385             390             395             400

Asp Ile Ala Val Glu Trp Glu Ser Asn Gly Gln Pro Glu Asn Asn Tyr
             405             410             415

Lys Thr Thr Pro Pro Val Leu Asp Ser Asp Gly Ser Phe Phe Leu Tyr
             420             425             430

Ser Lys Leu Thr Val Asp Lys Ser Arg Trp Gln Gln Gly Asn Val Phe
         435             440             445

Ser Cys Ser Val Met His Glu Ala Leu His Asn His Tyr Thr Gln Lys
    450             455             460

Ser Leu Ser Leu Ser Pro Gly Lys
465             470
```

<210> SEQ ID NO 13
<211> LENGTH: 702
<212> TYPE: DNA
<213> ORGANISM: artificial
<220> FEATURE:
<223> OTHER INFORMATION: DNA sequence encoding the light chain of
      chimeric 3G4

<400> SEQUENCE: 13

```
atgggatggt catgtatcat cctttttcta gtagcaactg caaccggtgt acattccgat      60
attgtcctca ctcaaagtcc ctcctcaatt agcgcctctc ttggcgatag gataaccatc     120
acatgccaag ctactcagga catcatcaag aacctgaact ggtatcagca gaaacctggc     180
aaaccaccga gcttcctcat ctactatgcg acagaagtgg cagaaggggt tcctagcaga     240
ttctctgggt ctggatcagg cagtgactat tccctgacca tatccaatct ggaaagcgag     300
gattttgccg actactactg tctgcagttc tacgagtttc cctatacgtt tggtggtgga     360
```

```
accaagttgg agattaagcg tacggtggct gcaccatctg tcttcatctt cccgccatct      420
gatgagcagt tgaaatctgg aactgcctct gttgtgtgcc tgctgaataa cttctatccc      480
agagaggcca aagtacagtg gaaggtggat aacgccctcc aatcgggtaa ctcccaggag      540
agtgtcacag agcaggacag caaggacagc acctacagcc tcagcagcac cctgacgctg      600
agcaaagcag actacgagaa acacaaagtc tacgcctgcg aagtcaccca tcagggcctg      660
agctcgcccg tcacaaagag cttcaacagg ggagagtgtt ag                        702
```

<210> SEQ ID NO 14
<211> LENGTH: 1419
<212> TYPE: DNA
<213> ORGANISM: artificial
<220> FEATURE:
<223> OTHER INFORMATION: DNA sequence encoding the heavy chain of
      chimeric 3G4

<400> SEQUENCE: 14

```
atgggatggt catgtatcat cctttttcta gtagcaactg caaccggtgt acattccgag       60
gtgcaactgc aggaaagtgg agcagaactc gttcgacctg gttcctcagt gaaactgagc      120
tgtaagccat ctgggtatac cttcatccgc aattggatcc attgggtcaa acagaggccc      180
atacagggac ttgagtggat tggagccatt gatccgtctg atggggaaag ccactacaac      240
cacaagttta cggacaaagc caccttgacc gtggataagt cctccagcac aggctatatg      300
cagctgaaca gcctgacaag tgaggactct gctgtgtact actgcaccag atcacggtat      360
tatggcggcg attgggactg gtacttcgac gtttggggta ctgggactac tgtcacagta      420
tccagcgcgt cgaccaaggg cccatcggtc ttccccctgg caccctcctc caagagcacc      480
tctgggggca gcgcggccct gggctgcctg gtcaaggact acttccccga acctgtgacg      540
gtctcgtgga actcaggcgc cctgaccagc ggcgtgcaca ccttcccggc tgtcctacag      600
tcctcaggac tctactccct cagcagcgtg gtgaccgtgc cctccagcag cttgggcacc      660
cagacctaca tctgcaacgt gaatcacaag cccagcaaca ccaaggtgga caagagagtt      720
gagcccaaat cttgtgacaa aactcacaca tgcccaccgt gcccagcacc tgaactcctg      780
gggggaccgt cagtcttcct cttccccca aaacccaagg acaccctcat gatctcccgg       840
acccctgagg tcacatgcgt ggtggtggac gtgagccacg aagaccctga ggtcaagttc      900
aactggtacg tggacggcgt ggaggtgcat aatgccaaga caaagccgcg ggaggagcag      960
tacaacagca cgtaccgtgt ggtcagcgtc ctcaccgtcc tgcaccagga ctggctgaat     1020
ggcaaggagt acaagtgcaa ggtctccaac aaagccctcc cagcccccat cgagaaaacc     1080
atctccaaag ccaaagggca gccccgagaa ccacaggtgt acaccctgcc cccatcccgg     1140
gaggagatga ccaagaacca ggtcagcctg acctgcctgg tcaaaggctt ctatcccagc     1200
gacatcgccg tggagtggga gagcaatggg cagccggaga caactacaa gaccacgcct      1260 cccgtgctgg actccgacgg ctccttcttc ctctatagca agctcaccgt ggacaagagc     1320
aggtggcagc aggggaacgt cttctcatgc tccgtgatgc atgaggctct gcacaaccac     1380
tacacgcaga gagcctctc cctgtccccg ggtaaatga                            1419
```

<210> SEQ ID NO 15
<211> LENGTH: 472
<212> TYPE: PRT
<213> ORGANISM: artificial
<220> FEATURE:
<223> OTHER INFORMATION: Heavy chain of chimeric 3G4 N297A Amino acid
      sequence

<400> SEQUENCE: 15

```
Met Gly Trp Ser Cys Ile Ile Leu Phe Leu Val Ala Thr Ala Thr Gly
1               5                   10                  15

Val His Ser Glu Val Gln Leu Gln Glu Ser Gly Ala Glu Leu Val Arg
            20                  25                  30

Pro Gly Ser Ser Val Lys Leu Ser Cys Lys Pro Ser Gly Tyr Thr Phe
        35                  40                  45

Ile Arg Asn Trp Ile His Trp Val Lys Gln Arg Pro Ile Gln Gly Leu
    50                  55                  60

Glu Trp Ile Gly Ala Ile Asp Pro Ser Asp Gly Glu Ser His Tyr Asn
65                  70                  75                  80

His Lys Phe Thr Asp Lys Ala Thr Leu Thr Val Asp Lys Ser Ser Ser
            85                  90                  95

Thr Gly Tyr Met Gln Leu Asn Ser Leu Thr Ser Glu Asp Ser Ala Val
            100                 105                 110

Tyr Tyr Cys Thr Arg Ser Arg Tyr Tyr Gly Gly Asp Trp Asp Trp Tyr
        115                 120                 125

Phe Asp Val Trp Gly Thr Gly Thr Thr Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
            165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
            195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
            245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Ala Ser Thr Tyr Arg Val Val Ser Val Leu Thr Val Leu His Gln
            325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
```

```
                405                  410                  415

Lys Thr Thr Pro Pro Val Leu Asp Ser Asp Gly Ser Phe Phe Leu Tyr
            420                  425                  430

Ser Lys Leu Thr Val Asp Lys Ser Arg Trp Gln Gln Gly Asn Val Phe
        435                  440                  445

Ser Cys Ser Val Met His Glu Ala Leu His Asn His Tyr Thr Gln Lys
    450                  455                  460

Ser Leu Ser Leu Ser Pro Gly Lys
465                  470
```

```
<210> SEQ ID NO 16
<211> LENGTH: 1419
<212> TYPE: DNA
<213> ORGANISM: artificial
<220> FEATURE:
<223> OTHER INFORMATION: DNA sequence encoding the heavy chain of
      chimeric 3G4 N297A

<400> SEQUENCE: 16
atgggatggt catgtatcat cctttttcta gtagcaactg caaccggtgt acattccgag      60
gtgcaactgc aggaaagtgg agcagaactc gttcgacctg ttcctcagt gaaactgagc     120 tgtaagccat ctgggtatac cttcatccgc aattggatcc attgggtcaa acagaggccc     180
atacagggac ttgagtggat tggagccatt gatccgtctg atggggaaag ccactacaac     240 cacaagtttta cggacaaagc caccttgacc gtggataagt cctccagcac aggctatatg     300
cagctgaaca gcctgacaag tgaggactct gctgtgtact actgcaccag atcacggtat     360
tatggcggcg attgggactg gtacttcgac gtttggggta ctgggactac tgtcacagta     420
tccagcgcgt cgaccaaggg cccatcggtc ttccccctgg cacccctcctc caagagcacc     480 tctggggggca gcgcggccct gggctgcctg gtcaaggact acttccccga acctgtgacg     540
gtctcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagagagtt     720
gagcccaaat cttgtgacaa aactcacaca tgcccaccgt gcccagcacc tgaactcctg     780 ggggggaccgt cagtcttcct cttcccccca aaacccaagg acaccctcat gatctcccgg     840
acccctgagg tcacatgcgt ggtggtggac gtgagccacg aagaccctga ggtcaagttc     900
aactggtacg tggacggcgt ggaggtgcat aatgccaaga caaagccgcg ggaggagcag     960
tacgccagca cgtaccgtgt ggtcagcgtc ctcaccgtcc tgcaccagga ctggctgaat    1020
ggcaaggagt acaagtgcaa ggtctccaac aaagccctcc agcccccat cgagaaaacc    1080 atctccaaag ccaaagggca gccccgagaa ccacaggtgt acaccctgcc cccatcccgg    1140
gaggagatga ccaagaacca ggtcagcctg acctgcctgg tcaaaggctt ctatcccagc    1200
gacatcgccg tggagtggga gagcaatggg cagccggaga caactacaa gaccacgcct    1260 cccgtgctgg actccgacgg ctccttcttc ctctatagca agctcaccgt ggacaagagc    1320
aggtggcagc aggggaacgt cttctcatgc tccgtgatgc atgaggctct gcacaaccac    1380
tacacgcaga gagcctctc cctgtccccg ggtaaatga                            1419
```

```
<210> SEQ ID NO 17
<211> LENGTH: 236
<212> TYPE: PRT
<213> ORGANISM: artificial
<220> FEATURE:
```

<223> OTHER INFORMATION: Amino Acid sequence of Fc RIIIA F158

<400> SEQUENCE: 17

```
Arg Thr Glu Asp Leu Pro Lys Ala Val Val Phe Leu Glu Pro Gln Trp
1               5                   10                  15

Tyr Arg Val Leu Glu Lys Asp Ser Val Thr Leu Lys Cys Gln Gly Ala
            20                  25                  30

Tyr Ser Pro Glu Asp Asn Ser Thr Gln Trp Phe His Asn Glu Ser Leu
        35                  40                  45

Ile Ser Ser Gln Ala Ser Ser Tyr Phe Ile Asp Ala Ala Thr Val Asp
    50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
            100                 105                 110

Trp Lys Asn Thr Ala Leu His Lys Val Thr Tyr Leu Gln Asn Gly Lys
            115                 120                 125

Gly Arg Lys Tyr Phe His His Asn Ser Asp Phe Tyr Ile Pro Lys Ala
        130                 135                 140

Thr Leu Lys Asp Ser Gly Ser Tyr Phe Cys Arg Gly Leu Phe Gly Ser
145                 150                 155                 160

Lys Asn Val Ser Ser Glu Thr Val Asn Ile Thr Ile Thr Gln Gly Leu
                165                 170                 175

Ala Val Ser Thr Ile Ser Ser Phe Phe Pro Pro Gly Tyr Gln Val Ser
                180                 185                 190

Phe Cys Leu Val Met Val Leu Leu Phe Ala Val Asp Thr Gly Leu Tyr
            195                 200                 205

Phe Ser Val Lys Thr Asn Ile Arg Ser Ser Thr Arg Asp Trp Lys Asp
        210                 215                 220

His Lys Phe Lys Trp Arg Lys Asp Pro Gln Asp Lys
225                 230                 235
```

```
<210> SEQ ID NO 18
<211> LENGTH: 236
<212> TYPE: PRT
<213> ORGANISM: artificial
<220> FEATURE:
<223> OTHER INFORMATION: Amino Acid sequence of Fc RIIIA V158
```

<400> SEQUENCE: 18

```
Arg Thr Glu Asp Leu Pro Lys Ala Val Val Phe Leu Glu Pro Gln Trp
1               5                   10                  15

Tyr Arg Val Leu Glu Lys Asp Ser Val Thr Leu Lys Cys Gln Gly Ala
            20                  25                  30

Tyr Ser Pro Glu Asp Asn Ser Thr Gln Trp Phe His Asn Glu Ser Leu
        35                  40                  45

Ile Ser Ser Gln Ala Ser Ser Tyr Phe Ile Asp Ala Ala Thr Val Asp
    50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
            100                 105                 110
```

-continued

```
Trp Lys Asn Thr Ala Leu His Lys Val Thr Tyr Leu Gln Asn Gly Lys
        115                 120                 125

Gly Arg Lys Tyr Phe His His Asn Ser Asp Phe Tyr Ile Pro Lys Ala
    130                 135                 140

Thr Leu Lys Asp Ser Gly Ser Tyr Phe Cys Arg Gly Leu Val Gly Ser
145                 150                 155                 160

Lys Asn Val Ser Ser Glu Thr Val Asn Ile Thr Ile Thr Gln Gly Leu
                165                 170                 175

Ala Val Ser Thr Ile Ser Ser Phe Phe Pro Pro Gly Tyr Gln Val Ser
                180                 185                 190

Phe Cys Leu Val Met Val Leu Leu Phe Ala Val Asp Thr Gly Leu Tyr
            195                 200                 205

Phe Ser Val Lys Thr Asn Ile Arg Ser Ser Thr Arg Asp Trp Lys Asp
        210                 215                 220

His Lys Phe Lys Trp Arg Lys Asp Pro Gln Asp Lys
225                 230                 235

<210> SEQ ID NO 19
<211> LENGTH: 215
<212> TYPE: PRT
<213> ORGANISM: artificial
<220> FEATURE:
<223> OTHER INFORMATION: Amino acid sequence of Fc RIIIB NA1

<400> SEQUENCE: 19

Arg Thr Glu Asp Leu Pro Lys Ala Val Val Phe Leu Glu Pro Gln Trp
1               5                   10                  15

Tyr Arg Val Leu Glu Lys Asp Ser Val Thr Leu Lys Cys Gln Gly Ala
            20                  25                  30

Tyr Ser Pro Glu Asp Asn Ser Thr Gln Trp Phe His Asn Glu Asn Leu
        35                  40                  45

Ile Ser Ser Gln Ala Ser Ser Tyr Phe Ile Asp Ala Ala Thr Val Asp
    50                  55                  60

Asp Ser Gly Glu Tyr Arg Cys Gln Thr Asn Leu Ser Thr Leu Ser Asp
65                  70                  75                  80

Pro Val Gln Leu Glu Val His Val Gly Trp Leu Leu Leu Gln Ala Pro
                85                  90                  95

Arg Trp Val Phe Lys Glu Glu Asp Pro Ile His Leu Arg Cys His Ser
            100                 105                 110

Trp Lys Asn Thr Ala Leu His Lys Val Thr Tyr Leu Gln Asn Gly Lys
        115                 120                 125

Asp Arg Lys Tyr Phe His His Asn Ser Asp Phe His Ile Pro Lys Ala
    130                 135                 140

Thr Leu Lys Asp Ser Gly Ser Tyr Phe Cys Arg Gly Leu Val Gly Ser
145                 150                 155                 160

Lys Asn Val Ser Ser Glu Thr Val Asn Ile Thr Ile Thr Gln Gly Leu
                165                 170                 175

Ala Val Ser Thr Ile Ser Ser Phe Ser Pro Pro Gly Tyr Gln Val Ser
                180                 185                 190

Phe Cys Leu Val Met Val Leu Leu Phe Ala Val Asp Thr Gly Leu Tyr
            195                 200                 205

Phe Ser Val Lys Thr Asn Ile
        210                 215

<210> SEQ ID NO 20
```

```
<211> LENGTH: 215
<212> TYPE: PRT
<213> ORGANISM: artificial
<220> FEATURE:
<223> OTHER INFORMATION: Amino acid sequence of Fc RIIIB NA2

<400> SEQUENCE: 20

Arg Thr Glu Asp Leu Pro Lys Ala Val Val Phe Leu Glu Pro Gln Trp
1               5                   10                  15

Tyr Ser Val Leu Glu Lys Asp Ser Val Thr Leu Lys Cys Gln Gly Ala
            20                  25                  30

Tyr Ser Pro Glu Asp Asn Ser Thr Gln Trp Phe His Asn Glu Ser Leu
        35                  40                  45

Ile Ser Ser Gln Ala Ser Ser Tyr Phe Ile Asp Ala Ala Thr Val Asn
    50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
            100                 105                 110

Trp Lys Asn Thr Ala Leu His Lys Val Thr Tyr Leu Gln Asn Gly Lys
        115                 120                 125

Asp Arg Lys Tyr Phe His His Asn Ser Asp Phe His Ile Pro Lys Ala
    130                 135                 140

Thr Leu Lys Asp Ser Gly Ser Tyr Phe Cys Arg Gly Leu Val Gly Ser
145                 150                 155                 160

Lys Asn Val Ser Ser Glu Thr Val Asn Ile Thr Ile Thr Gln Gly Leu
                165                 170                 175

Ala Val Ser Thr Ile Ser Ser Phe Ser Pro Pro Gly Tyr Gln Val Ser
                180                 185                 190

Phe Cys Leu Val Met Val Leu Leu Phe Ala Val Asp Thr Gly Leu Tyr
            195                 200                 205

Phe Ser Val Lys Thr Asn Ile
    210                 215

<210> SEQ ID NO 21
<211> LENGTH: 215
<212> TYPE: PRT
<213> ORGANISM: artificial
<220> FEATURE:
<223> OTHER INFORMATION: Amino Acid sequence of Fc RIIIB SH

<400> SEQUENCE: 21

Arg Thr Glu Asp Leu Pro Lys Ala Val Val Phe Leu Glu Pro Gln Trp
1               5                   10                  15

Tyr Ser Val Leu Glu Lys Asp Ser Val Thr Leu Lys Cys Gln Gly Ala
            20                  25                  30

Tyr Ser Pro Glu Asp Asn Ser Thr Gln Trp Phe His Asn Glu Ser Leu
        35                  40                  45

Ile Ser Ser Gln Ala Ser Ser Tyr Phe Ile Asp Asp Ala Thr Val Asn
    50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
```

-continued

```
              100                105                110

Trp Lys Asn Thr Ala Leu His Lys Val Thr Tyr Leu Gln Asn Gly Lys
        115                120                125

Asp Arg Lys Tyr Phe His His Asn Ser Asp Phe His Ile Pro Lys Ala
    130                135                140

Thr Leu Lys Asp Ser Gly Ser Tyr Phe Cys Arg Gly Leu Val Gly Ser
145                150                155                160

Lys Asn Val Ser Ser Glu Thr Val Asn Ile Thr Ile Thr Gln Gly Leu
                165                170                175

Ala Val Ser Thr Ile Ser Ser Phe Ser Pro Pro Gly Tyr Gln Val Ser
                180                185                190

Phe Cys Leu Val Met Val Leu Leu Phe Ala Val Asp Thr Gly Leu Tyr
        195                200                205

Phe Ser Val Lys Thr Asn Ile
        210                215
```